United States Patent
Toyama et al.

(10) Patent No.: US 9,126,995 B2
(45) Date of Patent: Sep. 8, 2015

(54) METHOD FOR CATALYTIC ASYMMETRIC SYNTHESIS OF OPTICALLY ACTIVE ISOXAZOLINE COMPOUND AND OPTICALLY ACTIVE ISOXAZOLINE COMPOUND

(71) Applicant: NISSAN CHEMICAL INDUSTRIES, LTD., Tokyo (JP)

(72) Inventors: Ken-ichi Toyama, Funabashi (JP); Yuji Moriyama, Funabashi (JP); Kazutaka Matoba, Funabashi (JP); Manabu Yaosaka, Funabashi (JP); Eitatsu Ikeda, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/356,906

(22) PCT Filed: Nov. 8, 2012

(86) PCT No.: PCT/JP2012/078992
§ 371 (c)(1),
(2) Date: Aug. 1, 2014

(87) PCT Pub. No.: WO2013/069731
PCT Pub. Date: May 16, 2013

(65) Prior Publication Data
US 2014/0350261 A1 Nov. 27, 2014

(30) Foreign Application Priority Data
Nov. 8, 2011 (JP) .................................. 2011-244198

(51) Int. Cl.
| | | |
|---|---|---|
| *C07D 261/02* | (2006.01) | |
| *C07D 453/04* | (2006.01) | |
| *C07D 261/04* | (2006.01) | |
| *B01J 31/02* | (2006.01) | |
| *C07B 53/00* | (2006.01) | |

(52) U.S. Cl.
CPC ........... *C07D 453/04* (2013.01); *B01J 31/0239* (2013.01); *C07B 53/00* (2013.01); *C07D 261/04* (2013.01); *B01J 2231/34* (2013.01)

(58) Field of Classification Search
CPC .................................................... C07D 261/04
USPC ......................................... 548/240; 546/134
See application file for complete search history.

(56) References Cited

U.S. PATENT DOCUMENTS

2014/0206633 A1* 7/2014 Mulholland et al. ............ 514/29

FOREIGN PATENT DOCUMENTS

| | | |
|---|---|---|
| JP | A-2008-239611 | 10/2008 |
| JP | A-2011-051977 | 3/2011 |
| WO | WO 2005/085216 A1 | 9/2005 |
| WO | WO 2007/026965 A1 | 3/2007 |
| WO | WO 2007/074789 A1 | 7/2007 |
| WO | WO 2007/105814 A1 | 9/2007 |
| WO | WO 2009/001942 A1 | 12/2008 |
| WO | WO 2009/025983 A2 | 2/2009 |
| WO | WO 2009/035004 A1 | 3/2009 |
| WO | WO 2009/063910 A1 | 5/2009 |
| WO | WO 2009063910 * | 5/2009 ........... C07D 261/04 |
| WO | WO 2009/080250 A2 | 7/2009 |
| WO | WO 2009/126668 A2 | 10/2009 |
| WO | WO 2011/067272 A1 | 6/2011 |
| WO | WO 2011/104089 A1 | 9/2011 |

OTHER PUBLICATIONS

Matoba et al. Angew. Chem. Int. Edn. 2010, 49, 5762-5766.*

(Continued)

*Primary Examiner* — Nizal Chandrakumar
(74) *Attorney, Agent, or Firm* — Oliff PLC

(57) ABSTRACT

There is provided a method for catalytic asymmetric synthesis of optically active isoxazoline compound and an optically active isoxazoline compound. A method for catalytic asymmetric synthesis of optically active isoxazoline compound of a formula (6) including reacting an α,β-unsaturated carbonyl compound of a formula (1) and a hydroxylamine in a solvent in the presence of a base by adding a chiral phase transfer catalyst. An optically active isoxazoline compound of a formula (13) that can be synthesized by the method.

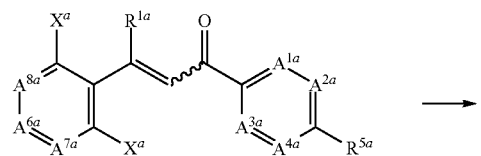

(1)

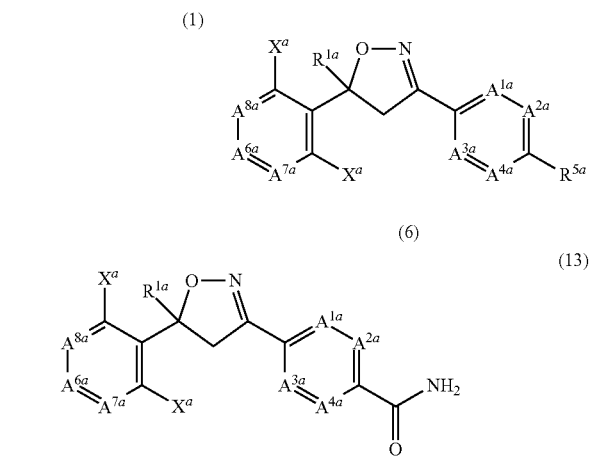

5 Claims, No Drawings

(56) References Cited

OTHER PUBLICATIONS

Matoba et al., "Enantioselective Synthesis of Trifluoromethyl-Substituted 2-Isoxazolines: Asymmetric Hydroxylamine/Enone Cascade Reaction," *Angew. Chem. Int. Ed.*, 2010, Vo. 49, pp. 5762-5766.

Dec. 11, 2012 Written Opinion issued in International Application No. PCT/JP2012/078992.

Dehmlow et al., "Monodeazacinchona Alkaloid Derivatives: Synthesis and Preliminary Applications as Phase-Transfer Catalysts," *Eur. J. Org. Chem.*, 2002, pp. 2087-2093.

Dec. 11, 2012 International Search Report issued in International Application No. PCT/JP2012/078992.

* cited by examiner

METHOD FOR CATALYTIC ASYMMETRIC SYNTHESIS OF OPTICALLY ACTIVE ISOXAZOLINE COMPOUND AND OPTICALLY ACTIVE ISOXAZOLINE COMPOUND

TECHNICAL FIELD

The present invention relates to a method for catalytic asymmetric synthesis of an optically active isoxazoline compound that is useful for production of medicines and agrochemicals, or functional materials such as electronic materials.

BACKGROUND ART

As a method for producing an optically active substance at the position 5 of a (4,5-dihydroisoxazol-3-yl)aryl compound, each of methods described in Patent Document 1 and Non Patent Document 1 has been known.

As a method for producing an optically active substance at the position 5 of a 4-(4,5-dihydroisoxazol-3-yl)benzoic acid compound, a production method according to a diastereomeric salt method has been known (see, for example, Patent Document 2).

As a method for producing an optically active substance at the position 5 of a 4-(4,5-dihydroisoxazol-3-yl)-N-thietan-3-yl-benzamide compound or a related compound, a method described in Patent Document 3 has been known.

As a general method, a method for preparing an optically active substance from a (4,5-dihydroisoxazol-3-yl)aryl compound that is a racemate has also been known, and in the method, optical resolution is conducted by using a column supporting an optically active carrier.

PRIOR ART DOCUMENTS

Patent Documents

Patent Document 1: WO 2009/063910
Patent Document 2: Japanese Patent Application Publication No. 2011-051977 (JP 2011-051977 A)
Patent Document 3: WO 2011/104089

Non-Patent Documents

Non-Patent Document 1: Angewandte Chemie International Edition, 2010, Volume 49, Page 5762

SUMMARY OF THE INVENTION

Problem to be Solved by the Invention

In Patent Document 1, a method for producing an optically active substance at the position 5 of a (4,5-dihydroisoxazol-3-yl)aryl compound by using a catalytic asymmetric cyclization reaction is provided. In the method, raw materials for the catalytic asymmetric cyclization reaction are an α,β-unsaturated carbonyl compound and hydroxylamine, and a chiral phase transfer catalyst is used for the reaction. However, the maximum enantiomeric excess among those obtained in Examples was 78% ee, which allows further improvement on enantioselectivity.

In Non-Patent Document 1, the maximum enantioselectivity was a high percentage of 94% ee. However, in Synthesis Example in which S-enantiomer is synthesized in a substituent pattern having strong bioactivity, the enantioselectivity was dropped to 81% ee, and a range for substrate application was narrow, which allows further improvement.

In Patent Document 2, a method for producing an optically active substance at the position 5 of a 4-(4,5-dihydroisoxazol-3-yl)benzoic acid compound, according to a diastereomeric salt method is provided. However, in an optical resolution method such as a diastereomeric salt method, final yield does not exceed 50% even if yield in a synthesis stage is 100%, which allows further improvement in terms of economics and green sustainable chemistry.

In Patent Document 3, the maximum enantioselectivity was 90% ee; however, only one combination of a substrate and a chiral phase transfer catalyst was disclosed, from which a result exceeding 90% ee Was obtained, and a range for substrate application was narrow, which allows further improvement.

Also, optical resolution by using a column supporting an optically active carrier is not only having productivity less than that of a diastereomeric salt method, but also having final yield not exceeding 50% similarly to a diastereomeric salt method, which allows further improvement in terms of economics and green sustainable chemistry.

As stated above, none of existing general methods can be used for producing an optically active substance at the position 5 of a (4,5-dihydroisoxazol-3-yl)aryl compound with a wide range for substrate application, in a highly productive and highly enantioselective manner, by using an asymmetric source with a catalytic amount. Thus, there is still room for improvement.

Means for Solving the Problem

In view of the above situations, and as a result of intensive study, the inventors of the present invention found the following matters. By selecting a proper combination of a substrate that is an α,β-unsaturated carbonyl compound and a catalyst that is a chiral phase transfer catalyst, and by selecting a proper reaction condition, an optically active substance at the position 5 of various compounds having an amide moiety or a methyleneamino moiety on a side chain of a (4,5-dihydroisoxazol-3-yl)aryl compound can be manufactured highly productively and highly enantioselectively, by using an asymmetric source with a catalytic amount in an asymmetric cyclization reaction that uses an α, β-unsaturated carbonyl compound and hydroxylamine as starting materials, and uses a chiral phase transfer catalyst. Thus, the present invention has been completed.

Specifically, the present invention relates to [1] to [12] below.

[1]
A method for catalytic asymmetric synthesis of an optically active isoxazoline compound comprises:
causing an α,β-unsaturated carbonyl compound of Formula (1):

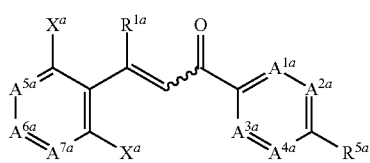

(1)

[where $R^{1a}$ is $C_{1-6}$ haloalkyl or $C_{3-8}$ halocycloalkyl;
each of $A^{1a}$, $A^{2a}$, $A^{3a}$, and $A^{4a}$ is independently N or $C-Y^a$;
each of $A^{5a}$, $A^{6a}$, and $A^{7a}$ is independently N or $C-X^a$;

$X^a$ is a hydrogen atom, a halogen atom, cyano, nitro, —SF$_5$, C$_{1-6}$ alkyl, C$_{1-6}$ haloalkyl, hydroxy(C$_{1-6}$)haloalkyl, C$_{1-6}$ alkoxy(C$_{1-6}$)haloalkyl, C$_{1-6}$ haloalkoxy(C$_{1-6}$)haloalkyl, C$_{3-8}$ halocycloalkyl, —OR$^{2a}$, —OSO$_2$R$^{2a}$, or —S(O)$_r$R$^{2a}$, and $X^a$s are optionally the same as or different from each other;

R$^{2a}$ is C$_{1-6}$ alkyl, C$_{1-4}$ alkoxy(C$_{1-4}$)alkyl, C$_{1-6}$ haloalkyl, or C$_{1-3}$ haloalkoxy(C$_{1-3}$)haloalkyl;

$Y^a$ is a hydrogen atom, a halogen atom, cyano, nitro, C$_{1-4}$ alkyl, C$_{1-4}$ haloalkyl, C$_{1-4}$ alkoxy, C$_{1-4}$ haloalkoxy, C$_{1-6}$ alkylthio, C$_{1-6}$ haloalkylthio, C$_{1-6}$ alkylsulfonyl, C$_{1-6}$ haloalkylsulfonyl, —NH$_2$, or —N(R$^{4a}$)R$^{3a}$, $Y^a$s are optionally the same as or different from each other, and when two $Y^a$s are adjacent to each other, the two $Y^a$s optionally form a 6-membered ring together with carbon atoms to which the two $Y^a$s are respectively bonded, by forming -A$^{8a}$=A$^{9a}$=A$^{10a}$=A$^{11a}$-;

each of A$^{8a}$, A$^{9a}$, A$^{10a}$, and A$^{11a}$ is independently N or C—Y$^{1a}$;

$Y^{1a}$ is a hydrogen atom, a halogen atom, cyano, nitro, C$_{1-4}$ alkyl, C$_{1-4}$ haloalkyl, C$_{1-4}$ alkoxy, C$_{1-4}$ haloalkoxy, C$_{1-6}$ alkylthio, C$_{1-6}$ haloalkylthio, C$_{1-6}$ alkylsulfonyl, C$_{1-6}$ haloalkylsulfonyl, —NH$_2$, or —N(R$^{4a}$)R$^{3a}$, and $Y^{1a}$s are optionally the same as or different from each other;

R$^{3a}$ is C$_{1-6}$ alkyl, —CHO, C$_{1-6}$ alkylcarbonyl, C$_{1-6}$ haloalkylcarbonyl, C$_{1-6}$ alkoxycarbonyl, C$_{1-6}$ alkylthiocarbonyl, C$_{1-6}$ alkoxythiocarbonyl, C$_{1-6}$ alkyldithiocarbonyl, C$_{1-6}$ alkylsulfonyl, or C$_{1-6}$ haloalkylsulfonyl;

R$^{4a}$ is a hydrogen atom or C$_{1-6}$ alkyl;

R$^{5a}$ is —C(O)NH$_2$, —C(O)NHR$^{6a}$, —C(S)NHR$^{6a}$, or -L-NHR$^{6a}$;

R$^{6a}$ is C$_{1-6}$ alkyl, C$_{1-6}$ alkyl optionally substituted with R$^{9a}$, C$_{3-6}$ cycloalkyl optionally condensed with a benzene ring, C$_{3-6}$ alkenyl, C$_{3-6}$ haloalkenyl, C$_{3-6}$ alkynyl, —N(R$^{11a}$)R$^{10a}$, —C(O)OR$^{12a}$, —C(O)NH$_2$, —C(O)NHR$^{12a}$, —C(R$^{14a}$)=NOR$^{13a}$, phenyl, phenyl substituted with (Z)$_{p1}$, D-5, D-7, D-10, D-11, D-12, D-14, D-15, D-18, D-31, D-32, D-42, D-43, D-45, D-46, D-48, E-1, E-2, E-3, E-4, E-7, E-9 to E-20 or E-21;

R$^{9a}$ is a halogen atom, cyano, amino, C$_{3-6}$ cycloalkyl, C$_{3-6}$ halocycloalkyl, C$_{1-6}$ alkoxy, C$_{1-6}$ haloalkoxy, C$_{1-6}$ alkylthio, C$_{1-6}$ haloalkylthio, C$_{1-6}$ alkylsulfinyl, C$_{1-6}$ haloalkylsulfinyl, C$_{1-6}$ alkylsulfonyl, C$_{1-6}$ haloalkylsulfonyl, —C(O)R$^{15a}$, —C(O)OR$^{15a}$, —C(O)NH$_2$, —C(O)N(R$^{16a}$)R$^{15a}$, —C(S)NH$_2$, —C(S)N(R$^{16a}$)R$^{15a}$, —C(R$^{18a}$)=NOR$^{17a}$, phenyl, phenyl substituted with (Z)$_{p1}$, D-1 to D-50, or E-1 to E-21;

D-1 to D-50 are heteroaromatic rings of structural formulae below:

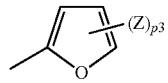
D-1

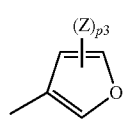
D-2

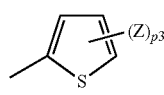
D-3

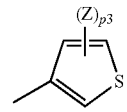
D-4

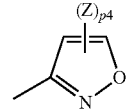
D-5

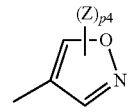
D-6

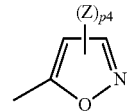
D-7

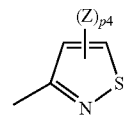
D-8

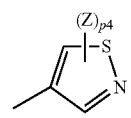
D-9

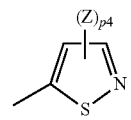
D-10

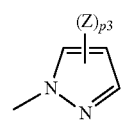
D-11

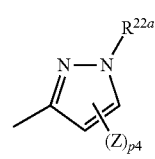
D-12

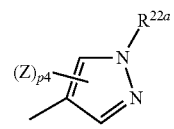
D-13

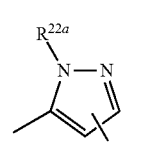
D-14

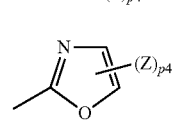
D-15

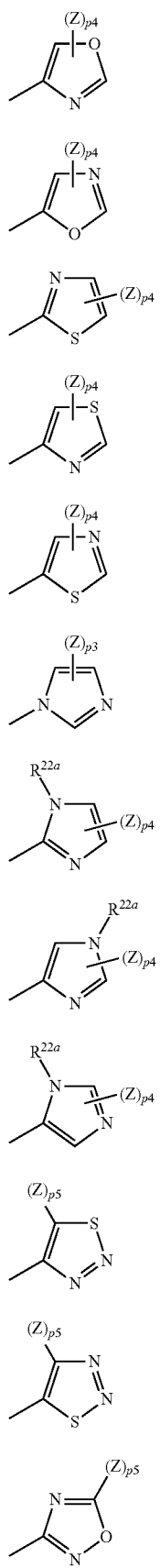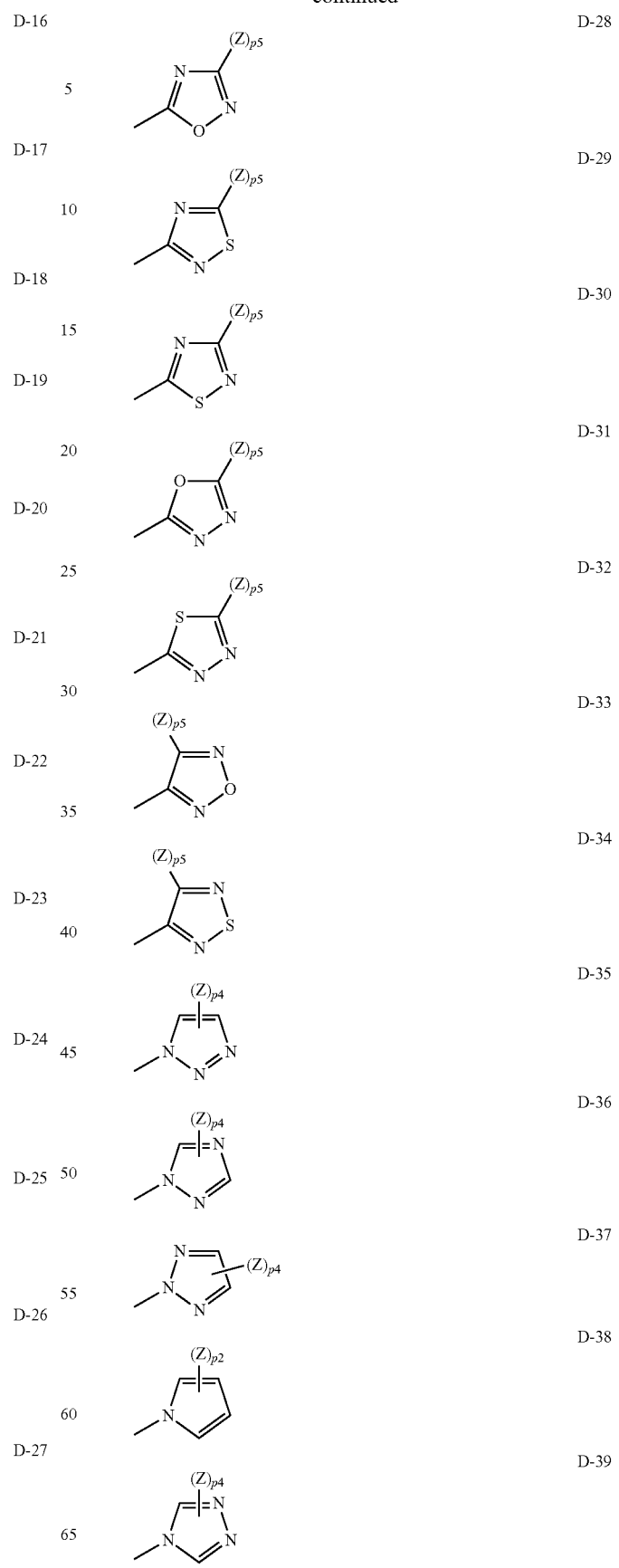

-continued

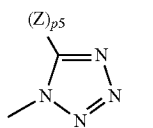
D-40

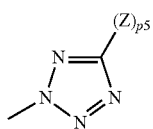
D-41

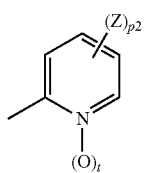
D-42

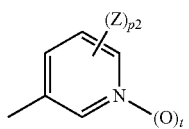
D-43

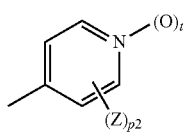
D-44

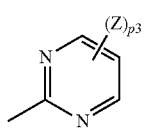
D-45

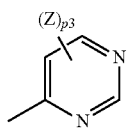
D-46

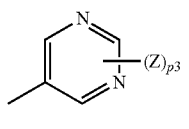
D-47

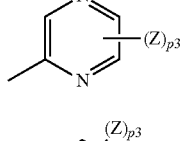
D-48

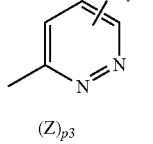
D-49

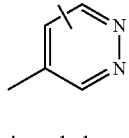
D-50

Z is a halogen atom, cyano, nitro, amino, $C_{1-6}$ alkyl, $(C_{1-6})$alkyl optionally substituted with $R^{19a}$, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ alkoxycarbonyl, —C(O)NH$_2$, —C(S)NH$_2$, —S(O)$_2$NH$_2$, —C(O)N(R$^{21a}$)R$^{20a}$, —C(S)N(R$^{21a}$)R$^{20a}$, $C_{1-6}$ alkylaminosulfonyl, or di($C_{1-6}$ alkyl)aminosulfonyl, and when p1, p2, p3, or p4 is an integer of 2 or more, Zs are optionally the same as or different from each other;

E-1 to E-21 are heterocycles of structural formulae below:

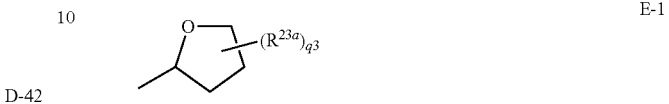
E-1

E-2

E-3

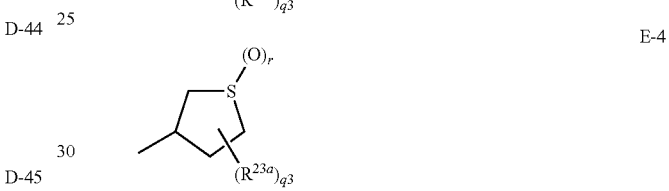
E-4

E-5

E-6

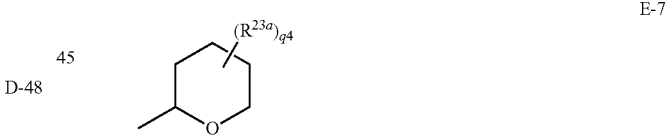
E-7

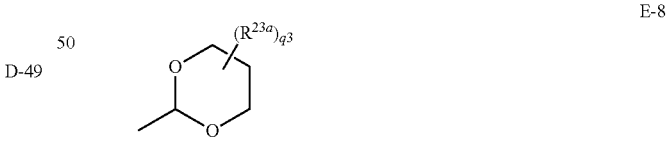
E-8

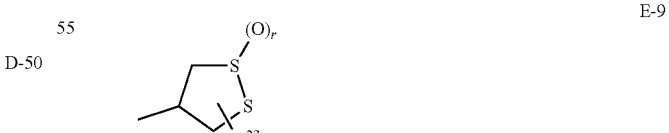
E-9

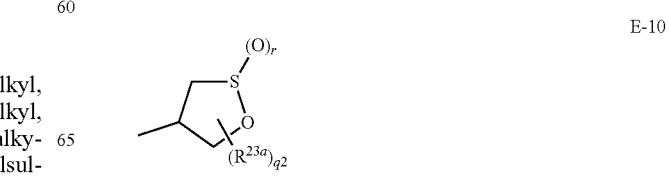
E-10

-continued

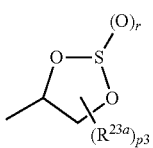
E-11

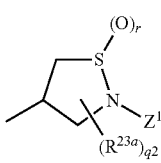
E-12

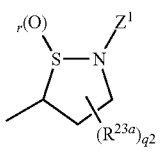
E-13

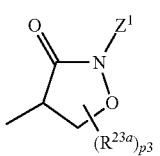
E-14

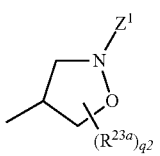
E-15

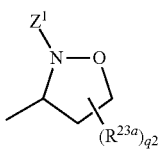
E-16

E-17

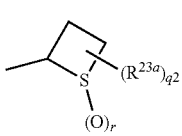
E-18

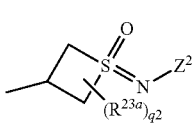
E-19

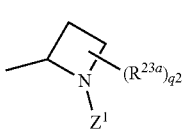
E-20

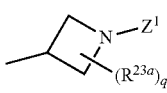
E-21

$Z^1$ is a hydrogen atom, $C_{1-6}$ alkyl, $C_{3-6}$ cycloalkyl, benzyl, ($C_{1-6}$)alkyl optionally substituted with $R^{19a}$, $C_{1-6}$ haloalkyl, $C_{1-6}$ alkylcarbonyl, $C_{1-6}$ haloalkylcarbonyl, phenylcarbonyl, phenylcarbonyl substituted with $(Z)_{p1}$, $C_{1-6}$ alkoxycarbonyl, $C_{1-6}$ alkylsulfinyl, $C_{1-6}$ haloalkylsulfinyl, $C_{1-6}$ alkylsulfonyl, $C_{1-6}$ haloalkylsulfonyl, —C(O)NH$_2$, —C(S)NH$_2$, —S(O)$_2$NH$_2$, —C(O)N(R$^{21a}$)R$^{20a}$, —C(S)N(R$^{21a}$)R$^{20a}$, $C_{1-6}$ alkylaminosulfonyl, di($C_{1-6}$ alkyl)aminosulfonyl, E-17, or E-18;

$Z^2$ is a hydrogen atom or $C_{1-6}$ haloalkylcarbonyl;

$R^{10a}$ is a $C_{1-6}$ haloalkyl, —C(O)R$^{15a}$, —C(O)OR$^{15a}$, phenyl, phenyl substituted with $(Z)_{p1}$, D-3, D-4, D-18, D-42, D-45, D-46, D-48, or D-49;

$R^{11a}$ is a hydrogen atom, $C_{1-6}$ alkyl, or $C_{3-6}$ alkynyl;

$R^{12a}$ is $C_{1-6}$ alkyl; haloalkyl, $C_{1-6}$ alkoxy($C_{1-4}$)alkyl, $C_{1-6}$ alkylthio($C_{1-4}$)alkyl; $C_{3-8}$ cycloalkyl, $C_{3-6}$ alkenyl, or $C_{3-6}$ alkynyl;

$R^{13a}$ is a hydrogen atom, $C_{1-6}$ alkyl, $C_{1-6}$ haloalkyl, $C_{3-6}$ cycloalkyl, $C_{3-6}$ halocycloalkyl, $C_{3-6}$ alkenyl, $C_{3-6}$ haloalkenyl, $C_{3-6}$ alkynyl, $C_{3-6}$ haloalkynyl, phenyl, phenyl substituted with $(Z)_{p1}$, D-42, D-45 to D-49, E-1 to E-4, or E-7;

$R^{14a}$ is a hydrogen atom, $C_{1-6}$ alkyl, $C_{1-6}$ haloalkyl, $C_{1-6}$ alkoxy($C_{1-6}$)alkyl, alkylthio($C_{1-6}$)alkyl, $C_{3-6}$ cycloalkyl, or phenyl;

$R^{15a}$ is $C_{1-6}$ alkyl, $C_{1-6}$ haloalkyl, $C_{3-6}$ cycloalkyl($C_{1-4}$)alkyl, $C_{3-6}$ cycloalkyl, $C_{1-6}$ alkoxy($C_{1-6}$)alkyl, hydroxy($C_{1-6}$)alkyl, phenyl, phenyl substituted with $R^{24a}$, $C_{3-6}$ haloalkenyl, $C_{3-6}$ alkenyl, or $C_{3-6}$ alkynyl;

$R^{24a}$ is a halogen atom, cyano, nitro, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ alkoxycarbonyl, —C(O)NH$_2$, —S(O)$_2$NH$_2$, $C_{1-6}$ alkylaminosulfonyl, or di($C_{1-6}$ alkyl)aminosulfonyl;

$R^{16a}$ is a hydrogen atom or $C_{1-6}$ alkyl;

$R^{19a}$ is hydroxy, $C_{1-4}$ alkoxy, or $C_{1-4}$ alkylthio;

$R^{20a}$ is a hydrogen atom, $C_{1-6}$ alkyl, $C_{3-6}$ cycloalkyl, $C_{3-6}$ alkenyl, $C_{3-6}$ haloalkenyl, $C_{3-6}$ alkynyl, —C(R$^{17a}$)=NOR$^{18a}$, —C(O)OR$^{18a}$, —C(O)NH$_2$, —C(O)N(R$^{17a}$)R$^{18a}$, —C(O)NHC(O)R$^{18a}$, —C(O)N(R$^{17a}$)C(O)OR$^{18a}$, —N(R$^{26a}$)R$^{25a}$, or phenyl;

$R^{17a}$ is a hydrogen atom or $C_{1-6}$ alkyl;

$R^{18a}$ is $C_{1-6}$ alkyl, $C_{1-6}$ haloalkyl, or $C_{2-6}$ alkenyl;

$R^{21a}$ is a hydrogen atom, $C_{1-6}$ alkyl, or $C_{3-6}$ alkynyl;

$R^{22a}$ is $C_{1-6}$ alkyl, phenyl, or phenyl substituted with $(Z)_{p1}$;

$R^{23a}$ is $C_{1-4}$ alkyl, and when q2, q3, or q4 is an integer of 2 or more, $R^{23a}$s are optionally the same as or different from each other, and further, when two of $R^{23a}$s exist on a single carbon atom as substituents, the two $R^{23a}$s optionally form an oxo together;

$R^{25a}$ is $C_{1-6}$ haloalkyl, $C_{1-6}$ alkoxycarbonyl, phenyl, phenyl substituted with $R^{27a}$, D-42 to D-46 or D-47;

$R^{27a}$ is a halogen atom, cyano, nitro, $C_{1-6}$ alkyl, $C_{1-6}$ haloalkyl, $C_{1-6}$ alkoxy, or $C_{1-6}$ alkylsulfonyl;

$R^{26a}$ is a hydrogen atom, $C_{1-6}$ alkyl, $C_{3-6}$ alkenyl, or $C_{3-6}$ alkynyl, p1 is an integer of 1 to 5;
p2 is an integer of 0 to 4;
p3 is an integer of 0 to 3;
p4 is an integer of 0 to 2;
p5 is an integer of 0 or 1;
q2 is an integer of 0 to 5;
q3 is an integer of 0 to 7;
q4 is an integer of 0 to 9;
t is an integer of 0 or 1;

L is —C(R$^{7a}$)(R$^{8a}$)—; —C(R$^{7a}$)(R$^{8a}$)CH$_2$—, or —CH$_2$C(R$^{7a}$)(R$^{8a}$)—;

$R^{7a}$ is a hydrogen atom, cyano, $C_{1-6}$ alkyl, $C_{1-6}$ haloalkyl, $C_{1-6}$ alkoxycarbonyl, —C(O)NH$_2$, or —C(S)NH$_2$;

$R^{8a}$ is a hydrogen atom or $C_{1-6}$ alkyl, or optionally forms a 3 to 6-membered ring together with carbon atoms bonded to a $C_{2-5}$ alkylene chain formed by $R^{7a}$ and $R^{8a}$, in which the alkylene chain optionally contains 1 to 3 oxygen atom(s), sulfur atom(s), or nitrogen atom(s); and r is an integer of 0 to 2]

to react with a hydroxylamine in a solvent, in the presence of a base and a chiral phase transfer catalyst of Formula (2), (3), (4), or (5):

(2)

(3)

(4)

(5)

[where $X^{1b-}$ is a negatively charged ion;

$R^{1b}$ is ethyl optionally substituted with $Y^b$, ethenyl optionally substituted with $Y^b$, oxiran-2-yl optionally substituted with $Y^b$, or 4,5-dihydroisoxazol-5-yl whose position 3 is optionally substituted with $Y^b$;

$R^{2b}$ is hydroxy, amino, $C_{1-6}$ alkoxy, or amino optionally substituted with $C_{1-6}$ alkyl;

$R^{3b}$ is a hydrogen atom or $C_{1-6}$ alkoxy;

$R^{4b}$ is a hydrogen atom or aryl optionally substituted with a halogen atom;

$Q^b$ is a nitrogen atom, a phosphorus atom, an arsenic atom, an antimony atom, a bismuth atom, or nitrogen oxide($N^+$—$O^-$);

each of $A^{1b}, A^{2b}, A^{3b}, A^{4b}, A^{5b}$, and $A^{6b}$ is independently N or C—$Y^b$;

$Y^b$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-6}$ alkylthio, $C_{1-6}$ haloalkylthio, $C_{1-6}$ alkylsulfonyl, $C_{1-6}$ haloalkylsulfonyl, —$NH_2$, or —$N(R^{4c})R^{3c}$, and $Y^b$s are optionally the same as or different from each other, and further, two adjacent $Y^b$s optionally form -$A^{7b}$=$A^{8b}$-$A^{9b}$=$A^{10b}$- as to form a 6-membered ring together with carbon atoms to which the two $Y^b$s are respectively bonded;

each of $A^{7b}, A^{8b}, A^{9b}$, and $A^{10b}$ is independently N or C—$Y^{1b}$;

$Y^{1b}$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-6}$ alkylthio, $C_{1-6}$ haloalkylthio, $C_{1-6}$ alkylsulfonyl, $C_{1-6}$ haloalkylsulfonyl, —$NH_2$, or —$N(R^{4c})R^{3c}$, and $Y^{1b}$s are optionally the same as or different from each other;

$R^{3c}$ is $C_{1-6}$ alkyl, —CHO, $C_{1-6}$ alkylcarbonyl, $C_{1-6}$ haloalkylcarbonyl, alkoxycarbonyl, $C_{1-6}$ alkylthiocarbonyl, $C_{1-6}$ alkoxythiocarbonyl, $C_{1-6}$ alkyldithiocarbonyl, $C_{1-6}$ alkylsulfonyl, or $C_{1-6}$ haloalkylsulfonyl; and $R^{4c}$ is a hydrogen atom or $C_{1-6}$ alkyl], in which the optically active isoxazoline compound is represented by Formula (6):

(6)

[where each of $R^{1a}, R^{5a}, X^a, A^{1a}, A^{2a}, A^{3a}, A^{4a}, A^{5a}, A^{6a}$, and $A^{7a}$ is the same as that described above].

[2]

In the method for catalytic asymmetric synthesis of an optically active isoxazoline compound, according to [1], in Formula (1), $R^{6a}$ is $C_{1-6}$ alkyl, $C_{1-6}$ alkyl optionally substituted with $R^{9a}$, $C_{3-6}$ cycloalkyl optionally condensed with a benzene ring, $C_{3-6}$ alkenyl, $C_{3-6}$ haloalkenyl, $C_{3-6}$ alkynyl, —$N(R^{11a})R^{10a}$, —$C(O)OR^{12a}$, —$C(O)NH_2$, —$C(O)NHR^{12a}$, —$C(R^{14a})$=$NOR^{13a}$, phenyl, phenyl substituted with $(Z)_{p1}$, D-5, D-7, D-10, D-11, D-12, D-14, D-15, D-18, D-31, D-32, D-42, D-43, D-45, D-46, D-48, E-1, E-2, E-3, E-4, E-7, E-9 to E-16, E-19, E-20, or E-21; and $R^{9a}$ is a halogen atom, cyano, amino, $C_{3-6}$ cycloalkyl, $C_{3-6}$ halocycloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, —$C(O)R^{15a}$, —$C(O)OR^{15a}$, —$C(O)NH_2$, —$C(O)N(R^{16a})R^{15a}$, —C(S)

$NH_2$, $-C(S)N(R^{16a})R^{15a}$, $-C(R^{18a})=NOR^{17a}$, phenyl, phenyl substituted with $(Z)_{p1}$, D-1 to D-50, E-1 to E-16, E-19, E-20 or E-21.

[3]

In the method for catalytic asymmetric synthesis of an optically active isoxazoline compound, according to [1], in Formula (1), $R^{1a}$ is $-CF_3$;

each of $A^{1a}$ and $A^{2a}$ is $C-Y^a$;

$Y^a$ is a hydrogen atom, or two adjacent $Y^a$s form $-CH=CH-CH=CH-$ so as to form a 6-membered ring together with carbon atoms to which the two $Y^a$s are respectively bonded;

$A^{3a}$ is CH;

$A^{4a}$ is CH or $C-CH_3$;

$R^{6a}$ is $C_{1-6}$ alkyl, $C_{1-6}$ alkyl optionally substituted with $R^{9a}$, $C_{3-6}$ cycloalkyl optionally condensed with a benzene ring, $C_{3-6}$ alkenyl, $C_{3-6}$ haloalkenyl, $C_{3-6}$ alkynyl, $-N(R^{11a})R^{10a}$, $-C(O)OR^{12a}$, $-C(O)NH_2$, $-C(O)NHR^{12a}$, $-C(R^{14a})=NOR^{13a}$, phenyl, phenyl substituted with $(Z)_{p1}$, D-5, D-7, D-10, D-11, D-12, D-14, D-15, D-18, D-31, D-32, D-42, D-43, D-45, D-46, D-48, E-1, E-2, E-3, E-4, E-7, E-9 to E-16, E-19, E-20, or E-21; and $R^{9a}$ is a halogen atom, cyano, amino, $C_{3-6}$ cycloalkyl, $C_{3-6}$ halocycloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $-C(O)R^{15a}$, $-C(O)OR^{15a}$, $-C(O)NH_2$, $-C(O)N(R^{16a})R^{15a}$, $-C(S)NH_2$, $-C(S)N(R^{16a})R^{15a}$, $-C(R^{18a})=NOR^{17a}$, phenyl, phenyl substituted with $(Z)_{p1}$, D-1 to D-50, E-1 to E-16, E-19, E-20 or E-21.

[4]

In the method for catalytic asymmetric synthesis of an optically active isoxazoline compound, according to any one of [1] to [3], in Formulae (2), (3), (4), and (5), each of $A^{1b}$ and $A^{2b}$ is $C-Y^b$, and two adjacent $Y^b$s form $-A^{7b}=A^{8b}-A^{9b}=A^{10b}-$ so as to form a 6-membered ring together with carbon atoms to which the two $Y^b$s are respectively bonded; and each of $A^{7b}$, $A^{8b}$, $A^{9b}$, and $A^{10b}$ is independently N or $C-Y^{1b}$.

[5]

In the method for catalytic asymmetric synthesis of an optically active isoxazoline compound, according to [1], in Formula (1), $R^{6a}$ is $C_1$ alkyl optionally substituted with $R^{9a}$, E-17, or E-18; and $R^{9a}$ is E-17 or E-18; and in Formulae (2), (3), (4), and (5), each of $A^{1b}$ and $A^{2b}$ is $C-Y^b$, and two adjacent $Y^b$s form $-A^{7b}=A^{8b}-A^{9b}=A^{10b}-$ so as to form a 6-membered ring together with carbon atoms to which the two $Y^b$s are respectively bonded; and each of $A^{7b}$, $A^{8b}$, $A^{9b}$, and $A^{10b}$ is independently N or $C-Y^{1b}$.

[6]

In the method for catalytic asymmetric synthesis of an optically active isoxazoline compound, according to any one of [1] to [5], in Formulae (2), (3), (4), and (5), $R^{1b}$ is ethyl, ethenyl, or 4,5-dihydroisoxazol-5-yl whose position 3 is optionally substituted with $Y^b$;

$R^{2b}$ is hydroxy;

$R^{4b}$ is a hydrogen atom; and $Q^b$ is a nitrogen atom or nitrogen oxide ($N^+-O^-$).

[7]

In the method for catalytic asymmetric synthesis of an optically active isoxazoline compound, according to any one of [1] to [6], in Formulae (2), (3), (4), and (5), $X^{1b-}$ is a halogen ion, a hydroxide ion, a tetrafluoroborate, a hexafluorophosphate, an acetate, a triflate, a phenoxide or a sulfonic acid ion optionally substituted with a polystyrene.

[8]

An optically active isoxazoline compound is represented by Formula (6):

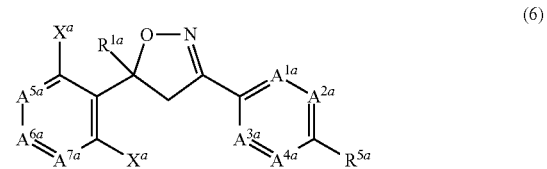

(6)

[where each of $R^{1a}$, $X^a$, $A^{1a}$, $A^{2a}$, $A^{3a}$, $A^{4a}$, $A^{5a}$, $A^{6a}$, and $A^{7a}$ is the same as that described in [1]; and $R^{5a}$ is $-C(O)NH_2$].

[9]

In the optically active isoxazoline compound according to [8], in Formula (6), $R^{1a}$ is $-CF_3$;

each of $A^{1a}$ and $A^{2a}$ is $C-Y^a$;

$Y^a$ is a hydrogen atom, or two adjacent $Y^a$s form $-CH=CH-CH=CH-$ so as to form a 6-membered ring together with carbon atoms to which the two $Y^a$s are respectively bonded;

$A^{3a}$ is CH; and $A^{4a}$ is CH or $C-CH_3$.

[10]

A chiral phase transfer catalyst is represented by Formula (2), (3), (4), or (5):

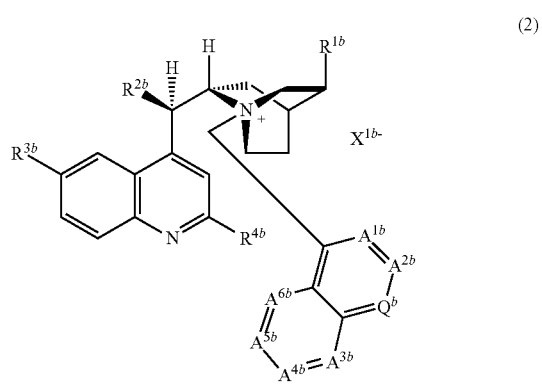

(2)

-continued

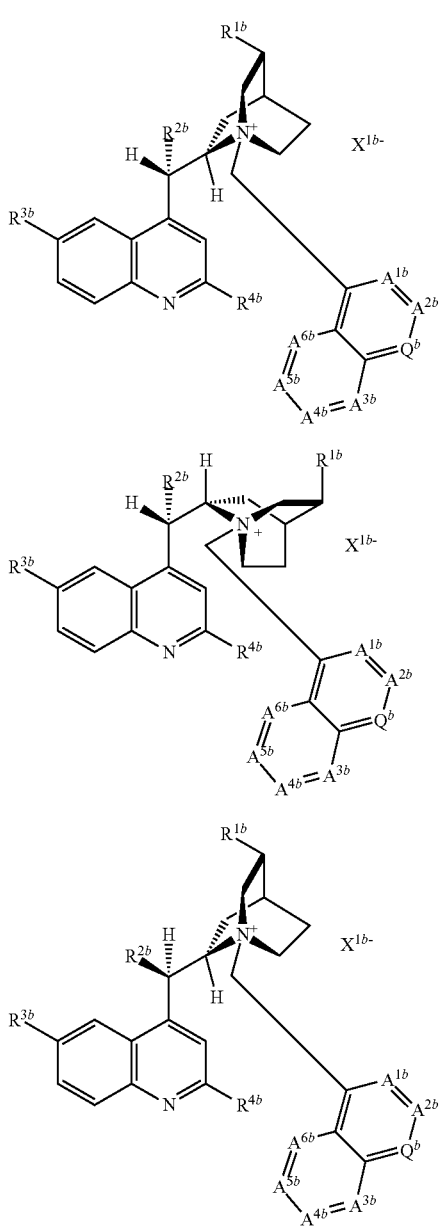

(3)

(4)

(5)

[where $X^{1b-}$ is a negatively charged ion;

$R^{1b}$ is ethyl optionally substituted with $Y^b$, ethenyl optionally substituted with $Y^b$, oxiran-2-yl optionally substituted with $Y^b$, or 4,5-dihydroisoxazol-5-yl whose position 3 is optionally substituted with $Y^b$;

$R^{2b}$ is hydroxy, amino, $C_{1-6}$ alkoxy, or amino optionally substituted with $C_{1-6}$ alkyl;

$R^{3b}$ is a hydrogen atom or $C_{1-6}$ alkoxy;

$R^{4b}$ is a hydrogen atom or aryl optionally substituted with a halogen atom;

$Q^b$ is a nitrogen atom, a phosphorus atom, an arsenic atom, an antimony atom, a bismuth atom, or nitrogen oxide($N^+$—$O^-$);

each of $A^{1b}$, $A^{2b}$, $A^{3b}$, $A^{4b}$, $A^{5b}$, and $A^{6b}$ is independently N or C—$Y^b$;

$Y^b$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-6}$ alkylthio, $C_{1-6}$ haloalkylthio, $C_{1-6}$ alkylsulfonyl, $C_{1-6}$ haloalkylsulfonyl, —$NH_2$, or —$N(R^{4c})R^{3c}$, and $Y^b$s are optionally the same as or different from each other, and further, two adjacent $Y^b$s optionally form -$A^{7b}$=$A^{8b}$-$A^{9b}$=$A^{10b}$- so as to form a 6-membered ring together with carbon atoms to which the two $Y^b$s are respectively bonded;

each of $A^{7b}$, $A^{8b}$, $A^{9b}$, and $A^{10b}$ is independently N or C—$Y^{1b}$;

$Y^{1b}$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-6}$ alkylthio, $C_{1-6}$ haloalkylthio, $C_{1-6}$ alkylsulfonyl, $C_{1-6}$ haloalkylsulfonyl, —$NH_2$, or —$N(R^{4c})R^{3c}$, and $Y^{1b}$s are optionally the same as or different from each other;

$R^{3c}$ is $C_{1-6}$ alkyl, —CHO, $C_{1-6}$ alkylcarbonyl, $C_{1-6}$ haloalkylcarbonyl, $C_{1-6}$ alkoxycarbonyl; $C_{1-6}$ alkylthiocarbonyl, $C_{1-6}$ alkoxythiocarbonyl, $C_{1-6}$ alkyldithiocarbonyl, $C_{1-6}$ alkylsulfonyl, or $C_{1-6}$ haloalkylsulfonyl; and $R^{4c}$ is a hydrogen atom or $C_{1-6}$ alkyl], {except for chiral phase transfer catalysts of Formulae (7) to (10):

(7)

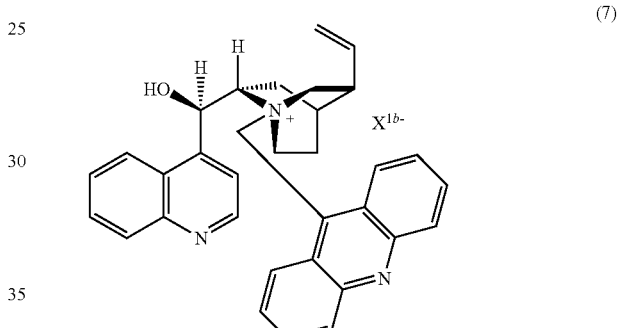

(8)

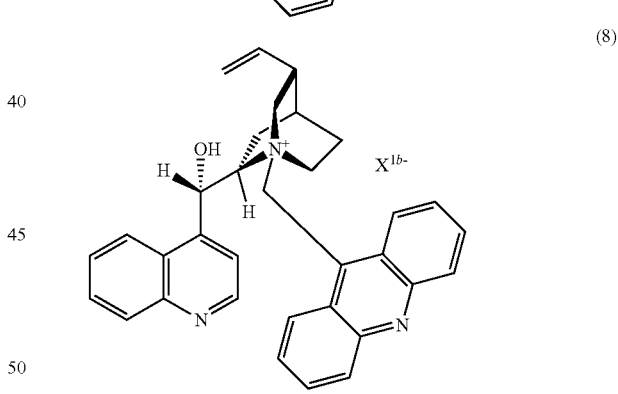

(9)

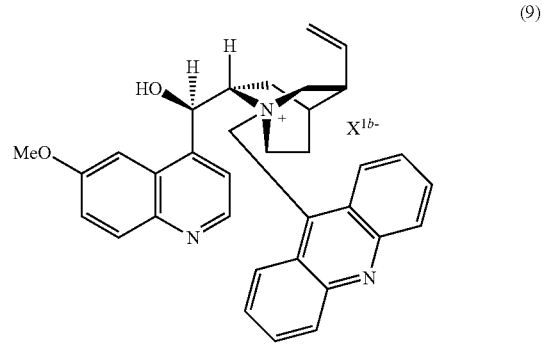

-continued (10)

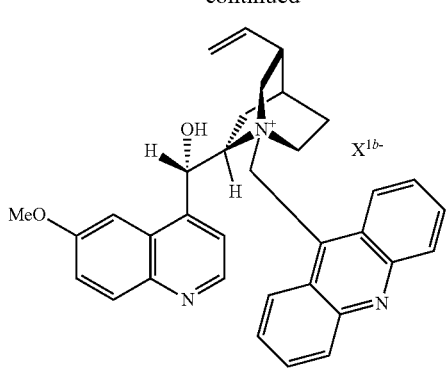

[where $X^{1b-}$ is a negatively charged ion]}.

[11]
In the chiral phase transfer catalyst according to [10],
$R^{2b}$ is hydroxy;
$R^{3b}$ is a hydrogen atom or methoxy;
$R^{4b}$ is a hydrogen atom;
$Q^b$ is a nitrogen atom, or nitrogen oxide ($N^+$—$O^-$);
$Y^b$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-6}$ alkylthio, $C_{1-6}$ haloalkylthio, $C_{1-6}$ alkylsulfonyl, $C_{1-6}$ haloalkylsulfonyl, —$NH_2$, or —$N(R^{4c})R^{3c}$, and $Y^b$s are optionally the same as or different from each other.

[12]
In the chiral phase transfer catalyst according to [10],
the chiral phase transfer catalyst is represented by Formula (11) or (12):

(11)

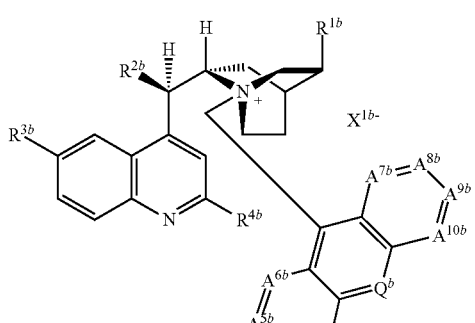

(12)

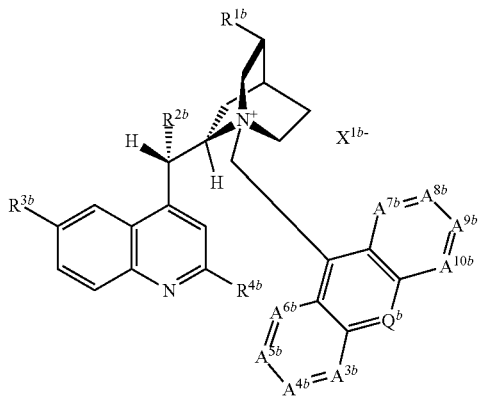

[where $R^{2b}$ is hydroxy;
$R^{3b}$ is a hydrogen atom or methoxy;
$R^{4b}$ is a hydrogen atom;
$Q^b$ is a nitrogen atom or nitrogen oxide ($N^+$—$O^-$);
each of $A^{3b}$, $A^{4b}$, $A^{5b}$, and $A^{6b}$ is C—$Y^b$;
$Y^b$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-6}$ alkylthio, $C_{1-6}$ haloalkylthio, $C_{1-6}$ alkylsulfonyl, $C_{1-6}$ haloalkylsulfonyl, —$NH_2$, or —$N(R^{4c})R^{3c}$, and $Y^b$s are optionally the same as or different from each other; and
each of $A^{7b}$, $A^{8b}$, $A^{9b}$, and $A^{10b}$ is C—$Y^{1b}$], {except for chiral phase transfer catalysts of Formulae (7) to (10):

(7)

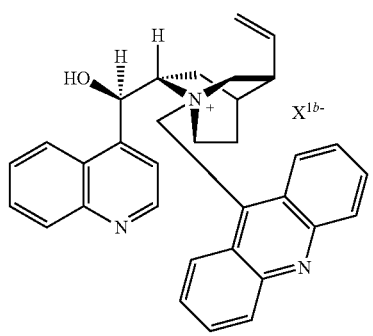

(8)

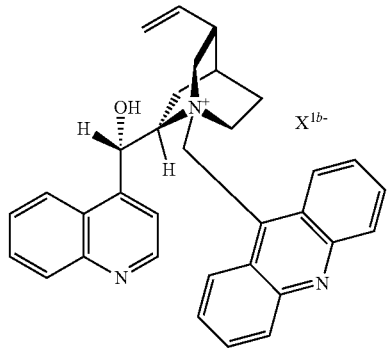

(9)

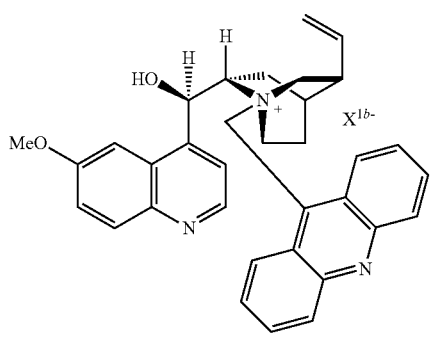

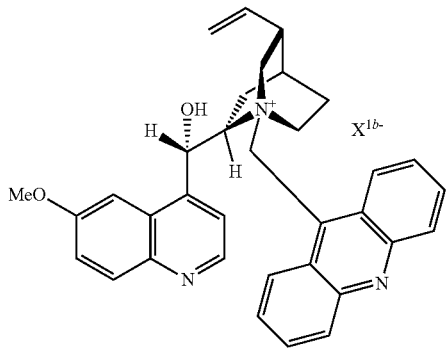

[where, $X^{1b-}$ is a negatively charged ion]}.

Effects of the Invention

The present invention can provide a novel optically active intermediate or final technical-grade product for an agrochemical, in particular, a compound having excellent insecticidal and acaricidal activities against pests in agriculture, spider mites, and endoparasites or ectoparasites of mammals or birds described in WO 05/085216, and a method for producing the same.

MODES FOR CARRYING OUT THE INVENTION

A compound of Formula (1) of the present specification has geometrical isomers including an E-isomer and a Z-isomer, and the present invention encompasses the E-isomer and the Z-isomer, or a mixture containing the E-isomer and the Z-isomer in any ratio. In addition, optically active substances resulting from one, or two or more asymmetric carbon atom(s) are included in a compound of Formula (4) of the present specification, and the compound described in the present specification encompasses all of the optically active substances and racemates.

Among compounds described in the present specification, examples of a compound that can be made into an acid addition salt by a conventional procedure include a salt of a hydrohalic acid, such as hydrofluoric acid, hydrochloric acid, hydrobromic acid, and hydroiodic acid; a salt of an inorganic acid, such as nitric acid, sulfuric acid, phosphoric acid, chloric acid, and perchloric acid; a salt of a sulfonic acid, such as methanesulfonic acid, ethanesulfonic acid, trifluoromethanesulfonic acid, benzenesulfonic acid, and p-toluenesulfonic acid; a salt of a carboxylic acid, such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid, and citric acid; and a salt of amino acid, such as glutamic acid and aspartic acid.

Among compounds described in the present specification, examples of a compound that can be made into a metal salt by a conventional procedure include a salt of an alkaline metal, such as lithium, sodium, and potassium; a salt of an alkaline earth metal, such as calcium, barium, and magnesium; and a salt of aluminum.

Specific examples of each of the substituents described in the present specification will be explained below. Here, n—means normal, i—means iso, s—means secondary, and t—means tertiary, and Ph means phenyl.

Examples of a halogen atom in a compound described in the present specification include a fluorine atom, a chlorine atom, a bromine atom, and an iodine atom. Note that the expression of "halo" in the present specification also refers to these halogen atoms.

The expression of $C_{a-b}$ alkyl in the present specification refers to a linear or branched hydrocarbon group having carbon atom(s) whose number is a to b. Specific examples of the $C_{a-b}$ alkyl include a methyl group, an ethyl group, a n-propyl group, an i-propyl group, a n-butyl group, an i-butyl group, a s-butyl group, a t-butyl group, a n-pentyl group, a 1-methylbutyl group, a 2-methylbutyl group, a 3-methylbutyl group; a 1-ethylpropyl group, a 1,1-dimethylpropyl group, a 1,2-dimethylpropyl group, a 2,2-dimethylpropyl group, a n-hexyl group, a 1-methylpentyl group, a 2-methylpentyl group, a 1,1-dimethylbutyl group, a 1,3-dimethylbutyl group, a heptyl group, an octyl group, a nonyl group, a decyl group, an undecyl group, and a dodecyl group, and the $C_{a-b}$ alkyl is selected within a range of the designated number of carbon atoms.

Specific examples of aryl described in the present specification include a phenyl group, a 1-naphthyl group, and a 2-naphthyl group.

Specific examples of heteroaryl group described in the present specification include a 2-thienyl group, a 3-thienyl group, a 2-furyl group, a 3-furyl group, a 2-pyranyl group, a 3-pyranyl group, a 4-pyranyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-iso benzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, an 8-chromenyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 1-indolizinyl group, a 2-indolizinyl group, a 3-indolizinyl group, a 5-indolizinyl group, a 6-indolizinyl group, a 7-indolizinyl group, an 8-indolizinyl group, a 1-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, an 8-purinyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 1-phthalazinyl group, a 5-phthalazinyl group, a 6-phthalazinyl group, a 2-naphthyridinyl group, a 3-naphthyridinyl group, a 4-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, an 8-quinazolinyl group, a 3-cinnolinyl group, a 4-cinnolinyl group, a 5-cinnolinyl group, a 6-cinnolinyl group, a 7-cinnolinyl group, an 8-cinnolinyl group, a 2-pteridinyl group, a 4-pteridinyl group, a 6-pteridinyl group, a 7-pteridinyl group, and a 3-furazanyl group.

The expression of $C_{a-b}$ haloalkyl in the present specification refers to a linear or branched hydrocarbon group having carbon atom(s) whose number is a to b, in which a hydrogen atom bonded to a carbon atom is optionally substituted with a halogen atom, and when the hydrocarbon group is substituted with two or more halogen atoms, these halogen atoms may be the same as or different from each other. Specific examples of the $C_{a-b}$ haloalkyl include a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a dibromofluoromethyl group, a 2-fluoroethyl group, a 2-chloroethyl group, a 2-bromoethyl group, a 2,2-difluoroethyl group, a 2-chloro-2-fluoroethyl group, a 2,2-dichloroethyl group, a 2-bromo-2-fluoroethyl group, a 2,2,2-trifluoroethyl group, a 2-chloro-2,2-difluoroethyl group, a 2,2-dichloro-2-fluoroethyl group, a 2,2,2-trichloroethyl group, a 2-bromo-2,2-difluoroethyl group, a 2-bromo-2-chloro-2-fluoroethyl group, a 2-bromo-2,2-dichloroethyl group, a 1,1,2,2-tetrafluoroethyl group, a pentafluoroethyl group, a 1-chloro-1,2,2,2-tetrafluoroethyl group, a 2-chloro-1,1,2,2-tetrafluoroethyl group, a 1,2-dichloro-1,2,2-trifluoroethyl group, a 2-bromo-1,1,2,2-tetrafluoroethyl group, a 2-fluoropropyl group, a 2-chloropropyl group, a 2-bromopropyl group, a 2-chloro-2-fluoropropyl group, a 2,3-dichloropropyl group, a 2-bromo-3-fluoropropyl group, a 3-bromo-2-chloropropyl group, a 2,3-dibromopropyl group, a 3,3,3-trifluoropropyl group, a 3-bromo-3,3-difluoropropyl group, a 2,2,3,3-tetrafluoropropyl group, a 2-chloro-3,3,3-trifluoropropyl group, a 2,2,3,3,3-pentafluoropropyl group, a 1,1,2,3,3,3-hexafluoropropyl group, a heptafluoropropyl group, a 2,3-dichloro-1,1,2,3,3-pentafluoropropyl group, a 2-fluoro-1-methylethyl group, a 2-chloro-1-methylethyl group, a 2-bromo-1-methylethyl group, a 2,2,2-trifluoro-1-(trifluoromethyl)ethyl group, a 1,2,2,2-tetrafluoro-1-(trifluoromethyl)ethyl group, a 2-fluorobutyl group, a 2-chlorobutyl group, a 2,2,3,3,4,4-hexafluorobutyl group, a 2,2,3,4,4,4-hexafluorobutyl group, a 2,2,3,3,4,4-hexafluorobutyl group, a 2,2,3,3,4,4,4-heptafluorobutyl group, a 1,1,2,2,3,3,4,4-octafluorobutyl group, a nonafluorobutyl group, a 4-chloro-1,1,2,2,3,3,4,4-octafluorobutyl group, a 2-fluoro-2-methylpropyl group, a 1,2,2,3,3,3-hexafluoro-1-(trifluoromethyl)propyl group, a 2-chloro-1,1-dimethylethyl group, a 2-bromo-1,1-dimethylethyl group, a 5-chloro-2,2,3,4,4,5,5-heptafluoropentyl group, and a tridecafluorohexyl group, and the $C_{a-b}$ haloalkyl is selected within a range of the designated number of carbon atoms.

The expression of $C_{a-b}$ cycloalkyl in the present specification refers to a cyclic hydrocarbon group having carbon atom(s) whose number is a to b, and the $C_{a-b}$ cycloalkyl can form a monocyclic structure or a polycyclic structure that has 3- to 6-membered ring(s). In addition, each of the rings may optionally be substituted with an alkyl group within a range of the designated number of carbon atoms. Specific examples of the $C_{a-b}$ cycloalkyl include a cyclopropyl group, a 1-methylcyclopropyl group, a 2-methylcyclopropyl group, a 2,2-dimethylcyclopropyl group, a 2,2,3,3-tetramethylcyclopropyl group, a cyclobutyl group, a cyclopentyl group, a 2-methylcyclopentyl group, a 3-methylcyclopentyl group, a cyclohexyl group, a 2-methylcyclohexyl-group, a 3-methylcyclohexyl group, a 4-methylcyclohexyl group, and a bicyclo [2.2.1]heptane-2-yl group. The $C_{a-b}$ cycloalkyl is selected within a range of the designated number of carbon atoms.

The expression of $C_{a-b}$ halocycloalkyl in the present specification refers to a $C_{a-b}$ cyclic hydrocarbon group having a carbon atom(s) whose number is of a to b, in which a hydrogen atom bonded to a carbon atom is optionally substituted with a halogen atom, and the $C_{a-b}$ halocycloalkyl can form a monocyclic structure or a polycyclic structure that has 3- to 6-membered ring(s). In addition, each of the rings may optionally be substituted with an alkyl group within a range of the designated number of carbon atoms, and the substitution by a halogen atom may occur on a ring structure, on a side chain, or on both of them, and when the cyclic hydrocarbon group is substituted with two or more halogen atoms, these halogen atoms may be the same as or different from each other. Specific examples of the $C_{a-b}$ halocycloalkyl include a 2,2-difluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 2,2,3,3-tetrafluorocyclobutyl group, a 2-(trifluoromethyl)cyclohexyl group, a 3-(trifluoromethyl)cyclohexyl group, and a 4-(trifluoromethyl)cyclohexyl group, and the $C_{a-b}$ halocycloalkyl is selected within a range of the designated number of carbon atoms.

The expression of $C_{a-b}$ alkenyl in the present specification refers to a linear or branched unsaturated hydrocarbon group having a carbon atom number of a to b, and having one, or two or more double bonds in a molecule. Specific examples of the $C_{a-b}$ alkenyl include a vinyl group, a 1-propenyl group, a 2-propenyl group, a 1-methylethenyl group, a 2-butenyl group, a 1-methyl-2-propenyl group, a 2-methyl-2-propenyl group, a 2-pentenyl group, a 2-methyl-2-butenyl group, a 3-methyl-2-butenyl group, a 2-ethyl-2-propenyl group, a 1,1-dimethyl-2-propenyl group, a 2-hexenyl group, a 2-methyl-2-pentenyl group, a 2,4-dimethyl-2,6-heptadienyl group, and a 3,7-dimethyl-2,6-octadienyl group, and the $C_{a-b}$ alkenyl is selected within a range of the designated number of carbon atoms.

The expression of $C_{a-b}$ haloalkenyl in the present specification refers to a linear or branched unsaturated hydrocarbon group having a carbon atom number of a to b, in which a hydrogen atom bonded to a carbon atom is optionally substituted with a halogen atom, and having one, or two or more double bonds in a molecule. When the unsaturated hydrocarbon group is optionally substituted with two or more halogen atoms, these halogen atoms may be the same as or different from each other. Specific examples of the $C_{a-b}$ haloalkenyl include a 2,2-dichlorovinyl group, a 2-fluoro-2-propenyl group, a 2-chloro-2-propenyl group, a 3-chloro-2-propenyl group, a 2-bromo-2-propenyl group, a 3-bromo-2-propenyl group, a 3,3-difluoro-2-propenyl group, a 2,3-dichloro-2-propenyl group, a 3,3-dichloro-2-propenyl group, a 2,3-dibromo-2-propenyl group, a 2,3,3-trifluoro-2-propenyl group, a 2,3,3-trichloro-2-propenyl group, a 1-(trifluoromethyl) ethenyl group, a 3-chloro[A1]-2-butenyl group, a 3-bromo-2-butenyl group, a 4,4-difluoro-3-butenyl group, a 3,4,4-trifluoro-3-butenyl group, a 3-chloro-4,4,4-trifluoro-2-butenyl group, and a 3-bromo-2-methyl-2-propenyl group, and the $C_{a-b}$ haloalkenyl is selected within a range of the designated number of carbon atoms.

The expression of $C_{a-b}$ alkynyl in the present specification refers to a linear or branched unsaturated hydrocarbon group having a carbon atom number of a to b, and having one, or two or more triple bonds in a molecule. Specific examples of the $C_{a-b}$ alkynyl include an ethynyl group, a 1-propynyl group, a 2-propynyl group, a 2-butynyl group, a 1-methyl-2-propynyl group, a 2-pentynyl group, a 1-methyl-2-butynyl group, a 1,1-dimethyl-2-propynyl group, and a 2-hexynyl group, and the $C_{a-b}$ alkynyl is selected within a range of the designated number of carbon atoms.

The expression of $C_{a-b}$ alkoxy in the present specification refers to a $C_{a-b}$ alkyl-O— group having a carbon atom(s) whose number is of a to b, in which the alkyl is as explained previously. Specific examples of the $C_{a-b}$ alkoxy include a methoxy group, an ethoxy group, a n-propyloxy group, an i-propyloxy group, a n-butyloxy group, an i-butyloxy group, a s-butyloxy group, a t-butyloxy group, a n-pentyloxy group, and a n-hexyloxy group, and the $C_{a-b}$ alkoxy is selected within a range of the designated number of carbon atoms.

The expression of $C_{a-b}$ haloalkoxy in the present specification refers to a $C_{a-b}$ haloalkyl-O— group having a carbon atom(s) whose number is of a to b, in which the haloalkyl is as explained previously. Specific examples of the $C_{a-b}$ haloalkoxy include a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2,-tetrafluoroethoxy group, a 2-chloro-1,1,2-trifluoroethoxy group, a 2-bromo-1,1,2-trifluoroethoxy group, a pentafluoroethoxy group, a 2,2-dichloro-1,1,2-trifluoroethoxy group, a 2,2,2-trichloro-1,1-difluoroethoxy group, a 2-bromo-1,1,2,2-tetrafluoroethoxy group, a 2,2,3,3-tetrafluoropropyloxy group, a 1,1,2,3,3,3-hexafluoropropyloxy group, a 2,2,2-trifluoro-1-(trifluoromethyl)ethoxy group, a heptafluoropropyloxy group, and a 2-bromo-1,1,2,3,3,3-hexafluoropropyloxy group, and the $C_{a-b}$ haloalkoxy is selected within a range of the designated number of carbon atoms.

The expression of $C_{a-b}$ alkylthio in the present specification refers to a $C_{a-b}$ alkyl-S— group having a carbon atom(s) whose number is of a to b, in which the alkyl is as explained previously. Specific examples of the $C_{a-b}$ alkylthio include a methylthio group, an ethylthio group, a n-propylthio group, an i-propylthio group, a n-butylthio group, an i-butylthio group, a s-butylthio group, a t-butylthio group, a n-pentylthio group, and a n-hexylthio group, and the $C_{a-b}$ alkylthio is selected within a range of the designated number of carbon atoms.

The expression of $C_{a-b}$ haloalkylthio in the present specification refers to a $C_{a-b}$ haloalkyl-S— group having a carbon atom(s) whose number is of a to b, in which the haloalkyl is as explained previously. Specific examples of the $C_{a-b}$ haloalkylthio include a difluoromethylthio group, a trifluoromethylthio group, a chlorodifluoromethylthio group, a bromodifluoromethylthio group, a 2,2,2-trifluoroethylthio group, a 1,1,2,2-tetrafluoroethylthio group, a 2-chloro-1,1,2-trifluoroethylthio group, a pentafluoroethylthio group, a 2-bromo-1,1,2,2-tetrafluoroethylthio group, a 1,1,2,3,3,3-hexafluoropropylthio group, a heptafluoropropylthio group, a 1,2,2,2-tetrafluoro-1-(trifluoromethyl)ethylthio group, and a nonafluorobutylthio group, and the $C_{a-b}$ haloalkylthio is selected within a range of the designated number of carbon atoms.

The expression of $C_{a-b}$ alkylsulfinyl in the present specification refers to a $C_{a-b}$ alkyl-S(O)— group having a carbon atom(s) whose number is of a to b, in which the alkyl is as explained previously. Specific examples of the $C_{a-b}$ alkylsulfinyl include a methylsulfinyl group, an ethylsulfinyl group, a n-propylsulfinyl group, an i-propylsulfinyl group, a n-butylsulfinyl group, an i-butylsulfinyl group, a s-butylsulfinyl group, and a t-butylsulfinyl group, and the $C_{a-b}$ alkylsulfinyl is selected within a range of the designated number of carbon atoms.

The expression of $C_{a-b}$ haloalkylsulfinyl in the present specification refers to a $C_{a-b}$ haloalkyl-S(O)— group having a carbon atom(s) whose number is of a to b, in which the haloalkyl is as explained previously. Specific examples of the $C_{a-b}$ haloalkylsulfinyl include a difluoromethylsulfinyl group, a trifluoromethylsulfinyl group, a chlorodifluoromethylsulfinyl group, a bromodifluoromethylsulfinyl group, a 2,2,2-trifluoroethylsulfinyl group, a 2-bromo-1,1,2,2-tetrafluoroethylsulfinyl group, a 1,2,2,2-tetrafluoro-1-(trifluoromethyl)ethylsulfinyl group, and a nonafluorobutylsulfinyl group, and the $C_{a-b}$ haloalkylsulfinyl is selected within a range of the designated number of carbon atoms.

The expression of $C_{a-b}$ alkylsulfonyl in the present specification refers to a $C_{a-b}$ alkyl-SO$_2$— group having a carbon atom(s) whose number is of a to b, in which the alkyl is as explained previously. Specific examples of the $C_{a-b}$ alkylsulfonyl include a methylsulfonyl group, an ethylsulfonyl group, a n-propylsulfonyl group, an i-propylsulfonyl group, a n-butylsulfonyl group, an i-butylsulfonyl group, a s-butylsulfonyl group, a t-butylsulfonyl group, a n-pentylsulfonyl group, and an n-hexylsulfonyl group, and the $C_{a-b}$ alkylsulfonyl is selected within a range of the designated number of carbon atoms.

The expression of $C_{a-b}$ haloalkylsulfonyl in the present specification refers to a $C_{a-b}$ haloalkyl-SO$_2$— group having a carbon atom(s) whose number is of a to b, in which the haloalkyl is as explained previously. Specific examples of the $C_{a-b}$ haloalkylsulfonyl include a difluoromethylsulfonyl group, a trifluoromethylsulfonyl group, a chlorodifluoromethylsulfonyl group, a bromodifluoromethylsulfonyl group, a 2,2,2-trifluoroethylsulfonyl group, a 1,1,2,2-tetrafluoroethylsulfonyl group, a 2-chloro-1,1,2-trifluoroethylsulfonyl group, and a 2-bromo-1,1,2,2-tetrafluoroethylsulfonyl group, and the $C_{a-b}$ haloalkylsulfonyl is selected within a range of the designated number of carbon atoms.

The expression of $C_{a-b}$ alkylcarbonyl in the present specification refers to a $C_{a-b}$ alkyl-C(O)— group having a carbon atom(s) whose number is of a to b, in which the alkyl is as explained previously. Specific examples of the $C_{a-b}$ alkylcarbonyl include an acetyl group, a propionyl group, a butyryl group, an isobutyryl group, a valeryl group, an isovaleryl group, a 2-methylbutanoyl group, a pivaloyl group, a hexanoyl group, and a heptanoyl group, and the $C_{a-b}$ alkylcarbonyl is selected within a range of the designated number of carbon atoms.

The expression of $C_{a-b}$ haloalkylcarbonyl in the present specification refers to a $C_{a-b}$ haloalkyl-C(O)— group having a carbon atom(s) whose number is of a to b, in which the haloalkyl is as explained previously. Specific examples of the $C_{a-b}$ haloalkylcarbonyl include a fluoroacetyl group, a chloroacetyl group, a difluoroacetyl group, a dichloroacetyl group, a trifluoroacetyl group, a chlorodifluoroacetyl group, a bromodifluoroacetyl group, a trichloroacetyl group, a penta fluoropropionyl group, a heptafluorobutanoyl group, and a 3-chloro-2,2-dimethylpropanoyl group, and the $C_{a-b}$ haloalkylcarbonyl is selected within a range of the designated number of carbon atoms.

The expression of $C_{a-b}$ alkoxycarbonyl in the present specification refers to a $C_{a-b}$ alkyl-O—C(O)— group having a carbon atom(s) whose number is of a to b, in which the alkyl is as explained previously. Specific examples of the $C_{a-b}$ alkoxycarbonyl include a methoxycarbonyl group, an ethoxycarbonyl group, a n-propyloxycarbonyl group, an i-propyloxycarbonyl group, a n-butoxycarbonyl group, an i-butoxycarbonyl group, and a t-butoxycarbonyl, and the $C_{a-b}$ alkoxycarbonyl is selected within a range of the designated number of carbon atoms.

The expression of $C_{a-b}$ alkylthiocarbonyl in the present specification refers to a $C_{a-b}$ alkyl-S—C(O)— group having a carbon atom(s) whose number is of a to b, in which the alkyl is as explained previously. Specific examples of the $C_{a-b}$ alkylthiocarbonyl include a methylthio-C(O)— group, an ethylthio-C(O)— group, a n-propylthio-C(O)— group, an i-propylthio-C(O)— group, a n-butylthio-C(O)— group, an i-butylthio-C(O)— group, and a t-butylthio-C(O)— group, and the $C_{a-b}$ alkylthiocarbonyl is selected within a range of the designated number of carbon atoms.

The expression of $C_{a-b}$ alkoxythiocarbonyl in the present specification refers to a $C_{a-b}$ alkyl-O—C(S)— group having a carbon atom(s) whose number is of a to b, in which the alkyl is as explained previously. Specific examples of the $C_{a-b}$ alkoxythiocarbonyl include a methoxy-C(S)— group, an ethoxy-C(S)— group, a n-propyloxy-C(S)— group, and an i-propyloxy-C(S)— group, and the $C_{a-b}$ alkoxythiocarbonyl is selected within a range of the designated number of carbon atoms.

The expression of $C_{a-b}$ alkyldithiocarbonyl in the present specification refers to a $C_{a-b}$ alkyl-S—C(S)— group having a carbon atom(s) whose number is of a to b, in which the alkyl is as explained previously. Specific examples of the $C_{a-b}$ alkyldithiocarbonyl include a methylthio-C(S)— group, an ethylthio-C(S)— group, a n-propylthio-C(S)— group, and an i-propylthio-C(S)— group, and the $C_{a-b}$ alkyldithiocarbonyl is selected within a range of the designated number of carbon atoms.

The expression of $C_{a-b}$ alkylaminosulfonyl in the present specification refers to a sulfamoyl group in which one of hydrogen atoms is substituted with a previously explained $C_{a-b}$ alkyl group having a carbon atom(s) whose number is of a to b. Specific examples of the $C_{a-b}$ alkylaminosulfonyl include a methylsulfamoyl group, an ethylsulfamoyl group, a n-propylsulfamoyl group, an i-propylsulfamoyl group, an n-butylsulfamoyl group, an i-butylsulfamoyl group, a s-butylsulfamoyl group, and a t-butylsulfamoyl group, and the $C_{a-b}$ alkylaminosulfonyl is selected within a range of the designated number of carbon atoms.

The expression of di($C_{a-b}$ alkyl)aminosulfonyl in the present specification refers to a sulfamoyl group in which each of two hydrogen atoms is substituted with a previously explained $C_{a-b}$ alkyl group having a carbon atom(s) whose number is of a to b, and the alkyl groups may be the same as or different from each other. Specific examples of the di($C_{a-b}$ alkyl)aminosulfonyl include a N,N-dimethylsulfamoyl group, an N-ethyl-N-methylsulfamoyl group; an N,N-diethylsulfamoyl group, an N,N-di-n-propylsulfamoyl group, and an N,N-di-n-butylsulfamoyl group, and the di($C_{a-b}$ alkyl)aminosulfonyl is selected within a range of the designated number of carbon atoms.

Each of the expressions of $C_{a-b}$ cycloalkyl($C_{d-e}$)alkyl, $C_{a-b}$ alkoxy($C_{d-e}$)alkyl, $C_{a-b}$ alkylthio($C_{d-e}$)alkyl. and the like in the present specification refers to a linear or branched hydrocarbon group having a carbon atom number of d to e, in which a hydrogen atom bonded to a carbon atom is optionally substituted with a $C_{a-b}$ cycloalkyl group, a $C_{a-b}$ alkoxy group, or a $C_{a-b}$ alkylthio group, which is explained previously, and each of the $C_{a-b}$ cycloalkyl($C_{d-e}$)alkyl, $C_{a-b}$ alkoxy($C_{d-e}$)alkyl, $C_{a-b}$ alkylthio($C_{d-e}$)alkyl, and the like is selected within a range of the designated number of carbon atoms.

The expression of ethyl optionally substituted with $Y^b$ in the present specification refers to an ethyl group in which a hydrogen atom bonded to a carbon atom is optionally substituted with any $Y^b$, and when the number of the substituent $Y^b$ on each of ethyl groups is two or more, the $Y^b$s may be the same as or different from each other.

The expression of ethenyl optionally substituted with $Y^b$ in the present specification refers to an ethenyl group in which a hydrogen atom bonded to a carbon atom is optionally substituted with any $Y^b$, and when the number of the substituent $Y^b$ on each of ethenyl groups is two or more, the $Y^b$s may be the same as or different from each other.

The expression of oxiran-2-yl optionally substituted with $Y^b$ in the present specification refers to an oxiran-2-yl group in which a hydrogen atom bonded to a carbon atom is optionally substituted with any $Y^b$, and when the number of the substituent $Y^b$ on each of oxiran-2-yl groups is two or more, the $Y^b$s may be the same as or different from each other.

The expression of 4,5-dihydroisoxazol-5-yl whose position 3 is optionally substituted with $Y^b$ in the present specification refers to a 4,5-dihydroisoxazol-5-yl group in which a hydrogen atom bonded to the position 3 is optionally substituted with any $Y^b$, and when the number of the substituent $Y^b$ on each of 4,5-dihydroisoxazol-5-yl groups is two or more, the $Y^b$s may be the same as or different from each other.

The expression of aryl optionally substituted with a halogen atom in the present specification refers to an aromatic hydrocarbon group in which a hydrogen atom bonded to a carbon atom is optionally substituted with a halogen atom, and when the number of the halogen atom on each of aryl groups is two or more, these halogen atoms may be the same as or different from each other.

The expression of a sulfonic acid ion optionally substituted with a polystyrene in the present specification refers to a sulfonic acid ion substituted with a linear or branched polystyrene, or substituted with an alkyl group or an aryl group instead of a polystyrene, and specific examples thereof include a sulfonated polystyrene resin ion disclosed in Journal of Synthetic Organic Chemistry, Japan, 67(10), 1025-1032, 2009, a methanesulfonic acid ion, a para-toluenesulfonic acid ion, and a trifluoromethanesulfonic acid ion.

The expression of a ($C_{a-b}$)alkyl optionally substituted with $R^{9a}$ in the present specification refers to a linear or branched hydrocarbon group having a carbon atom number of a to b, in which a hydrogen atom bonded to a carbon atom is optionally substituted with any $R^{9a}$. The ($C_{a-b}$)alkyl optionally substituted with $R^{9a}$ is selected within a range of the designated number of carbon atoms, and when the number of the substituent $R^{9a}$ on each of ($C_{a-b}$)alkyl groups is two or more, these $R^{9a}$s may be the same as or different from each other.

The expression of phenyl substituted with $(Z)_{p1}$ in the present specification refers to a phenyl group, in which a hydrogen atom bonded to a carbon atom is optionally substituted with any Z. When the number of the substituent Z on the phenyl group is two or more, these Zs may be the same as or different from each other.

The expression of a ($C_{a-b}$)alkyl optionally substituted with $R^{19a}$ in the present specification refers to a linear or branched hydrocarbon group having a carbon atom number of a to b, in which a hydrogen atom bonded to a carbon atom is optionally substituted with any $R^{19a}$. The ($C_{a-b}$)alkyl optionally substituted with $R^{19a}$ is selected within a range of the designated number of carbon atoms, and when the number of the substituent $R^{19a}$ on each of ($C_{a-b}$)alkyl groups is two or more, these $R^{19a}$s may be the same as or different from each other.

The expression of $C_{a-b}$ cycloalkyl optionally condensed with a benzene ring in the present specification refers to a $C_{a-b}$ cyclic hydrocarbon group, in which hydrogen atoms bonded to two adjacent carbon atoms are optionally substituted with a benzene ring, and a polycyclic structure that has 3 to 6-membered rings can be formed. Specific examples of the $C_{a-b}$ cycloalkyl optionally condensed with a benzene ring include a 1-indane group, a 2-indane group, a 1,2,3,4-tetrahydro-1-naphthalene group, and a 1,2,3,4-tetrahydro-2-naphthalene group, and the $C_{a-b}$ cycloalkyl optionally condensed with a benzene ring is selected within a range of the designated number of carbon atoms.

Each of the expression of hydroxy($C_{d-e}$)haloalkyl, $C_{a-b}$ alkoxy($C_{d-e}$)haloalkyl, and $C_{a-b}$ haloalkoxy($C_{d-e}$)haloalkyl in the present specification refers to a $C_{d-e}$ haloalkyl group having a carbon atom(s) whose number is of a to b, as explained previously, in which a hydrogen atom or a halogen atom bonded to a carbon atom is optionally substituted with a $C_{a-b}$ alkoxy group or a $C_{a-b}$ haloalkoxy group, which is explained previously, or a hydroxy group. Specific examples of the hydroxy($C_{d-e}$)haloalkyl, $C_{a-b}$ alkoxy($C_{d-e}$)haloalkyl, and $C_{a-b}$ haloalkoxy($C_{d-e}$)haloalkyl include a 2,2,2-trifluoro-1-hydroxy-1-(trifluoromethyl)ethyl group, a difluoro(methoxy)methyl group, a 2,2,2-trifluoro-1-methoxy-1-(trifluoromethyl)ethyl group, a difluoro(2,2,2-trifluoroethoxy)methyl group, a 2,2,2-trifluoro-1-(2,2,2-trifluoroethoxy)-1-(trifluoromethyl)ethyl group, and a 3-(1,2-dichloro-1,2,2-trifluoroethoxy)-1,1,2,2,3,3-hexafluoropropyl group, and each of the hydroxy($C_{d-e}$)haloalkyl, $C_{a-b}$ alkoxy($C_{d-e}$)haloalkyl, and $C_{a-b}$ haloalkoxy($C_{d-e}$)haloalkyl is selected within a range of the designated number of carbon atoms.

A solvent that can be used in a reaction of the present invention is not particularly limited as long as progress of the reaction is not inhibited. Examples of the solvent include aromatic hydrocarbons optionally substituted with halogen atoms, such as benzene, toluene, xylene, fluorobenzene, chlorobenzene, o-dichlorobenzene, and mesitylene; aliphatic hydrocarbons optionally substituted with halogen atoms, such as n-pentane, n-hexane, n-heptane, n-octane, cyclopentane, cyclohexane, methylene chloride, chloroform, and 1,2-dichloroethane, and methylcyclohexane; and ether solvents, such as diethyl ether, diisopropyl ether, di-n-butyl ether, cyclopentyl methyl ether, t-butyl methyl ether, t-butyl ethyl ether, tetrahydrofuran, dimethoxyethane, dioxane, and tetrahydropyran; and among them, toluene, xylene, fluorobenzene, chlorobenzene, o-dichlorobenzene, n-hexane, n-heptane, cyclohexane, methylene chloride, 1,2-dichloroethane, diisopropyl ether, cyclopentyl methyl ether, and t-butyl ethyl ether is preferable. These solvents may be used alone, or two or more of them may be used in combination.

Although the amount of the solvent used is not particularly limited, it is usually 0.1 part by mass to 100 parts by mass, preferably 0.5 part by mass to 50 parts by mass, and particularly preferably 1 part by mass to 15 parts by mass for 1 part by mass of an α,β-unsaturated carbonyl compound.

Hydroxylamine that can be used in a reaction of the present invention may be a salt of an acid, such as hydrochloride, sulfate, phosphate, oxalate, nitrate, and acetate; or may be an aqueous solution of either a free hydroxylamine or the salt.

The amount of the hydroxylamine used is usually 0.5 mol to 100 mol, preferably 1 mol to 10 mol, and particularly preferably 1 mol to 2 mol for 1 mol of an α,β-unsaturated carbonyl compound.

Examples of a chiral phase transfer catalyst that can be used in a reaction of the present invention include compounds listed in Table 1. Note that the compounds listed in Table 1 are for illustrative purposes, and the present invention is not limited thereto. In Table 1, compounds of Formulae (2) to (5), in which $X^{1b-}$ is a negatively charged ion, $R^{1b}$ is ethenyl, $R^{2b}$ is hydroxy, $R^{3b}$ is a hydrogen atom or methoxy, $R^{4b}$ is a hydrogen atom, $Q^b$ is a nitrogen atom, each of $A^{1b}$ and $A^{2b}$ is independently $C—Y^b$, the two adjacent $Y^b$s form -$A^{7b}$=$A^{8b}$- $A^{9b}$=$A^{10b}$- together, each of $A^{7b}$, $A^{8b}$, $A^{9b}$, and $A^{10b}$ is independently $C—Y^{1b}$, $Y^{1b}$ is a hydrogen atom, each of $A^{3b}$, $A^{4b}$, $A^{5b}$, and $A^{6b}$ is independently $C—Y^b$, and the $Y^b$ is a hydrogen atom (that is, A is A-1), are excluded from a chiral phase transfer catalyst defined in Claim 10.

In Table 1, a substituent expressed as Me is a methyl group, a substituent expressed as Ph is a phenyl group, a substituent expressed as OAc is an acetoxy group, a substituent expressed as OTf is a trifluoromethanesulfonyloxy group, a substituent expressed as OPh is a phenoxy group, and a substituent expressed as PS—$SO_3$ is a sulfonic acid group substituted with a polystyrene.

In the table, heteroaromatic rings of A-1 to A-8 are the following structures, respectively.

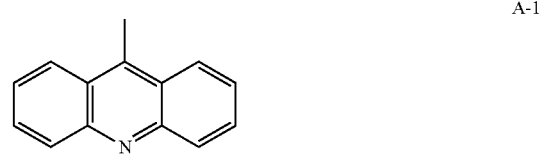

A-1

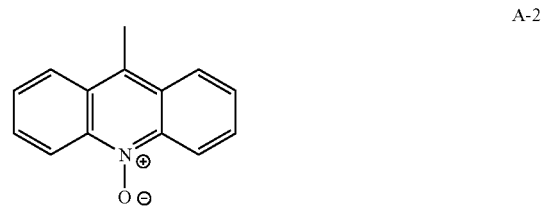

A-2

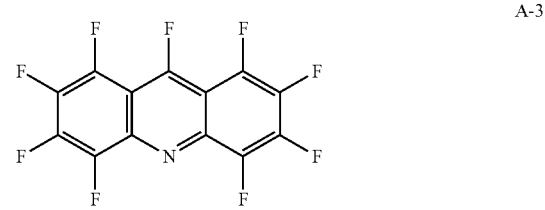

A-3

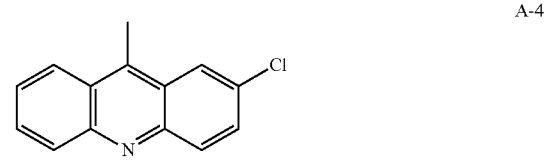

A-4

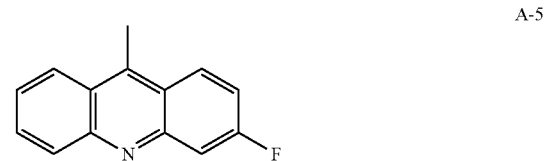

A-5

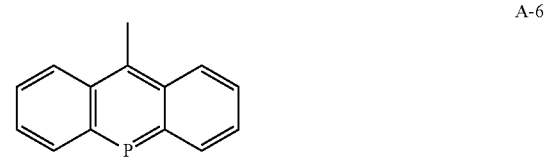

A-6

A-7

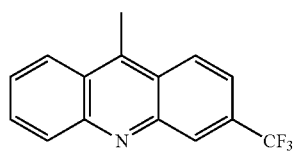
A-8
For example, A-1 is an acridin-9-yl group.
In the table, a substituent of $R^{1b}$-1 is the following structure.
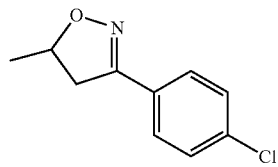
$R^{1b}$-1
$R^{1b}$-1 is a 3-(4-chlorophenyl)-4,5-dihydroisoxazol-5-yl group.
TABLE 1
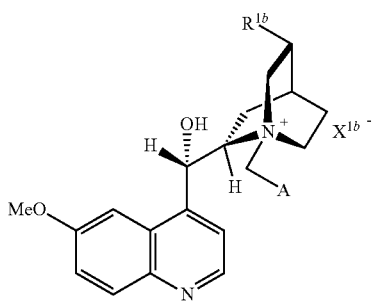
TABLE 1-continued
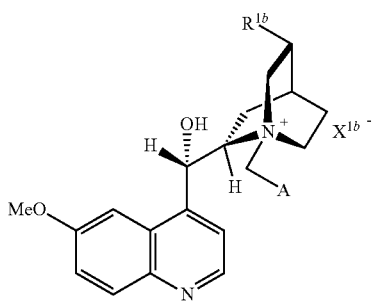
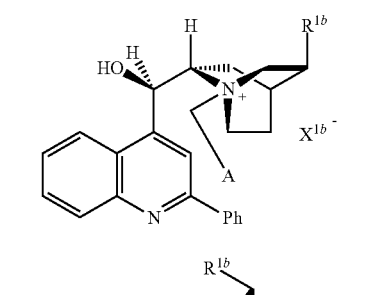
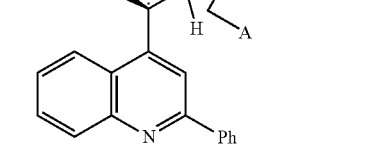
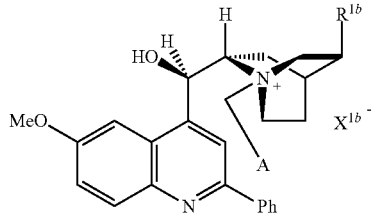
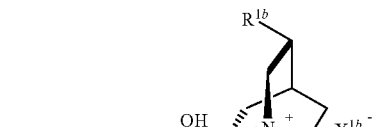
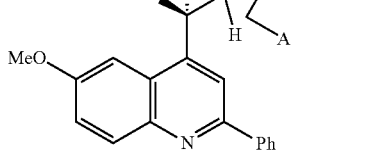
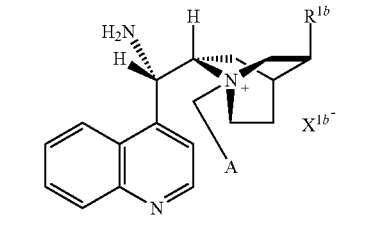

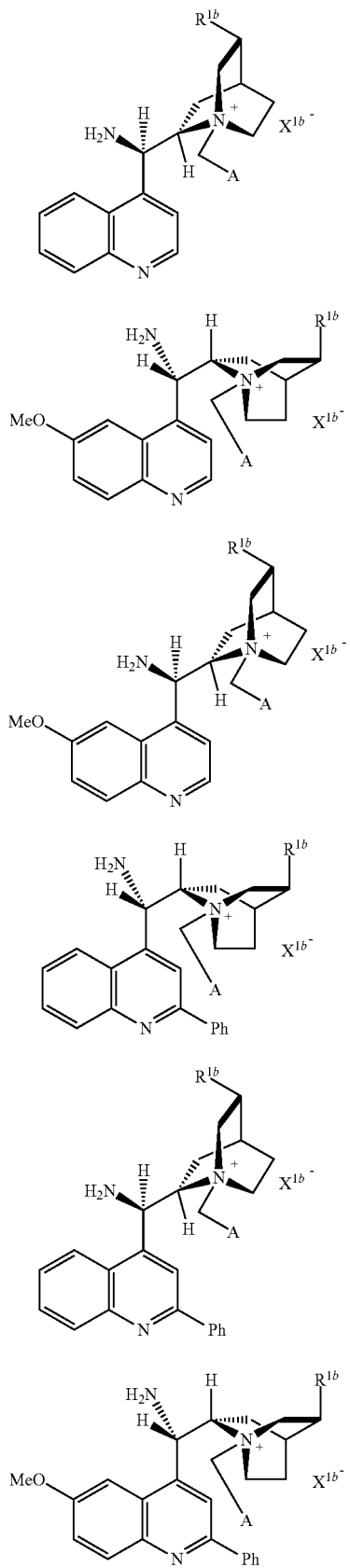

| A | $R^{1b}$ | $X^{1b}$ |
|---|---|---|
| A-1 | CH=CH$_2$ | Br |
| A-1 | CH=CH$_2$ | Cl |
| A-1 | CH=CH$_2$ | I |
| A-1 | CH=CH$_2$ | OH |
| A-1 | CH=CH$_2$ | OAc |
| A-1 | CH=CH$_2$ | OTf |
| A-1 | CH=CH$_2$ | OPh |
| A-1 | CH=CH$_2$ | BF$_4$ |
| A-1 | CH=CH$_2$ | PF$_6$ |
| A-1 | CH=CH$_2$ | PS—SO$_3$ |
| A-1 | CH$_2$—CH$_3$ | Br |
| A-1 | CH$_2$—CH$_3$ | Cl |
| A-1 | CH$_2$—CH$_3$ | I |
| A-1 | CH$_2$—CH$_3$ | OH |
| A-1 | CH$_2$—CH$_3$ | OAc |
| A-1 | CH$_2$—CH$_3$ | OTf |
| A-1 | CH$_2$—CH$_3$ | OPh |
| A-1 | CH$_2$—CH$_3$ | BF$_4$ |
| A-1 | CH$_2$—CH$_3$ | PF$_6$ |
| A-1 | CH$_2$—CH$_3$ | PS—SO$_3$ |
| A-1 | $R^{1b}$-1 | Br |
| A-1 | $R^{1b}$-1 | Cl |
| A-1 | $R^{1b}$-1 | I |
| A-1 | $R^{1b}$-1 | OH |
| A-1 | $R^{1b}$-1 | OAc |
| A-1 | $R^{1b}$-1 | OTf |
| A-1 | $R^{1b}$-1 | OPh |
| A-1 | $R^{1b}$-1 | BF$_4$ |
| A-1 | $R^{1b}$-1 | PF$_6$ |
| A-1 | $R^{1b}$-1 | PS—SO$_3$ |
| A-2 | CH=CH$_2$ | Br |
| A-2 | CH=CH$_2$ | Cl |
| A-2 | CH=CH$_2$ | I |
| A-2 | CH=CH$_2$ | OH |
| A-2 | CH=CH$_2$ | OAc |
| A-2 | CH=CH$_2$ | OTf |
| A-2 | CH=CH$_2$ | OPh |
| A-2 | CH=CH$_2$ | BF$_4$ |
| A-2 | CH=CH$_2$ | PF$_6$ |
| A-2 | CH=CH$_2$ | PS—SO$_3$ |
| A-2 | CH$_2$—CH$_3$ | Br |
| A-2 | CH$_2$—CH$_3$ | Cl |
| A-2 | CH$_2$—CH$_3$ | I |
| A-2 | CH$_2$—CH$_3$ | OH |
| A-2 | CH$_2$—CH$_3$ | OAc |
| A-2 | CH$_2$—CH$_3$ | OTf |
| A-2 | CH$_2$—CH$_3$ | OPh |
| A-2 | CH$_2$—CH$_3$ | BF$_4$ |
| A-2 | CH$_2$—CH$_3$ | PF$_6$ |
| A-2 | CH$_2$—CH$_3$ | PS—SO$_3$ |
| A-2 | $R^{1b}$-1 | Br |
| A-2 | $R^{1b}$-1 | Cl |
| A-2 | $R^{1b}$-1 | I |
| A-2 | $R^{1b}$-1 | OH |
| A-2 | $R^{1b}$-1 | OAc |
| A-2 | $R^{1b}$-1 | OTf |
| A-2 | $R^{1b}$-1 | OPh |
| A-2 | $R^{1b}$-1 | BF$_4$ |
| A-2 | $R^{1b}$-1 | PF$_6$ |

-continued

| A | $R^{1b}$ | $X^{1b}$ |
|---|---|---|
| A-2 | $R^{1b}$-1 | PS—SO$_3$ |
| A-3 | CH=CH$_2$ | Br |
| A-3 | CH=CH$_2$ | Cl |
| A-3 | CH=CH$_2$ | I |
| A-3 | CH=CH$_2$ | OH |
| A-3 | CH=CH$_2$ | OAc |
| A-3 | CH=CH$_2$ | OTf |
| A-3 | CH=CH$_2$ | OPh |
| A-3 | CH=CH$_2$ | BF$_4$ |
| A-3 | CH=CH$_2$ | PF$_6$ |
| A-3 | CH=CH$_2$ | PS—SO$_3$ |
| A-3 | CH$_2$—CH$_3$ | Br |
| A-3 | CH$_2$—CH$_3$ | Cl |
| A-3 | CH$_2$—CH$_3$ | I |
| A-3 | CH$_2$—CH$_3$ | OH |
| A-3 | CH$_2$—CH$_3$ | OAc |
| A-3 | CH$_2$—CH$_3$ | OTf |
| A-3 | CH$_2$—CH$_3$ | OPh |
| A-3 | CH$_2$—CH$_3$ | BF$_4$ |
| A-3 | CH$_2$—CH$_3$ | PF$_6$ |
| A-3 | CH$_2$—CH$_3$ | PS—SO$_3$ |
| A-3 | $R^{1b}$-1 | Br |
| A-3 | $R^{1b}$-1 | Cl |
| A-3 | $R^{1b}$-1 | I |
| A-3 | $R^{1b}$-1 | OH |
| A-3 | $R^{1b}$-1 | OAc |
| A-3 | $R^{1b}$-1 | OTf |
| A-3 | $R^{1b}$-1 | OPh |
| A-3 | $R^{1b}$-1 | BF$_4$ |
| A-3 | $R^{1b}$-1 | PF$_6$ |
| A-3 | $R^{1b}$-1 | PS—SO$_3$ |
| A-4 | CH=CH$_2$ | Br |
| A-4 | CH=CH$_2$ | Cl |
| A-4 | CH=CH$_2$ | I |
| A-4 | CH=CH$_2$ | OH |
| A-4 | CH=CH$_2$ | OAc |
| A-4 | CH=CH$_2$ | OTf |
| A-4 | CH=CH$_2$ | OPh |
| A-4 | CH=CH$_2$ | BF$_4$ |
| A-4 | CH=CH$_2$ | PF$_6$ |
| A-4 | CH=CH$_2$ | PS—SO$_3$ |
| A-4 | CH$_2$—CH$_3$ | Br |
| A-4 | CH$_2$—CH$_3$ | Cl |
| A-4 | CH$_2$—CH$_3$ | I |
| A-4 | CH$_2$—CH$_3$ | OH |
| A-4 | CH$_2$—CH$_3$ | OAc |
| A-4 | CH$_2$—CH$_3$ | OTf |
| A-4 | CH$_2$—CH$_3$ | OPh |
| A-4 | CH$_2$—CH$_3$ | BF$_4$ |
| A-4 | CH$_2$—CH$_3$ | PF$_6$ |
| A-4 | CH$_2$—CH$_3$ | PS—SO$_3$ |
| A-4 | $R^{1b}$-1 | Br |
| A-4 | $R^{1b}$-1 | Cl |
| A-4 | $R^{1b}$-1 | I |
| A-4 | $R^{1b}$-1 | OH |
| A-4 | $R^{1b}$-1 | OAc |
| A-4 | $R^{1b}$-1 | OTf |
| A-4 | $R^{1b}$-1 | OPh |
| A-4 | $R^{1b}$-1 | BF$_4$ |
| A-4 | $R^{1b}$-1 | PF$_6$ |
| A-4 | $R^{1b}$-1 | PS—SO$_3$ |
| A-5 | CH=CH$_2$ | Br |
| A-5 | CH=CH$_2$ | Cl |
| A-5 | CH=CH$_2$ | I |
| A-5 | CH=CH$_2$ | OH |
| A-5 | CH=CH$_2$ | OAc |
| A-5 | CH=CH$_2$ | OTf |
| A-5 | CH=CH$_2$ | OPh |
| A-5 | CH=CH$_2$ | BF$_4$ |
| A-5 | CH=CH$_2$ | PF$_6$ |
| A-5 | CH=CH$_2$ | PS—SO$_3$ |
| A-5 | CH$_2$—CH$_3$ | Br |
| A-5 | CH$_2$—CH$_3$ | Cl |
| A-5 | CH$_2$—CH$_3$ | I |
| A-5 | CH$_2$—CH$_3$ | OH |
| A-5 | CH$_2$—CH$_3$ | OAc |
| A-5 | CH$_2$—CH$_3$ | OTf |
| A-5 | CH$_2$—CH$_3$ | OPh |
| A-5 | CH$_2$—CH$_3$ | BF$_4$ |
| A-5 | CH$_2$—CH$_3$ | PF$_6$ |
| A-5 | CH$_2$—CH$_3$ | PS—SO$_3$ |
| A-5 | $R^{1b}$-1 | Br |
| A-5 | $R^{1b}$-1 | Cl |
| A-5 | $R^{1b}$-1 | I |
| A-5 | $R^{1b}$-1 | OH |
| A-5 | $R^{1b}$-1 | OAc |
| A-5 | $R^{1b}$-1 | OTf |
| A-5 | $R^{1b}$-1 | OPh |
| A-5 | $R^{1b}$-1 | BF$_4$ |
| A-5 | $R^{1b}$-1 | PF$_6$ |
| A-5 | $R^{1b}$-1 | PS—SO$_3$ |
| A-6 | CH=CH$_2$ | Br |
| A-6 | CH=CH$_2$ | Cl |
| A-6 | CH=CH$_2$ | I |
| A-6 | CH=CH$_2$ | OH |
| A-6 | CH=CH$_2$ | OAc |
| A-6 | CH=CH$_2$ | OTf |
| A-6 | CH=CH$_2$ | OPh |
| A-6 | CH=CH$_2$ | BF$_4$ |
| A-6 | CH=CH$_2$ | PF$_6$ |
| A-6 | CH=CH$_2$ | PS—SO$_3$ |
| A-6 | CH$_2$—CH$_3$ | Br |
| A-6 | CH$_2$—CH$_3$ | Cl |
| A-6 | CH$_2$—CH$_3$ | I |
| A-6 | CH$_2$—CH$_3$ | OH |
| A-6 | CH$_2$—CH$_3$ | OAc |
| A-6 | CH$_2$—CH$_3$ | OTf |
| A-6 | CH$_2$—CH$_3$ | OPh |
| A-6 | CH$_2$—CH$_3$ | BF$_4$ |
| A-6 | CH$_2$—CH$_3$ | PF$_6$ |
| A-6 | CH$_2$—CH$_3$ | PS—SO$_3$ |
| A-6 | $R^{1b}$-1 | Br |
| A-6 | $R^{1b}$-1 | Cl |
| A-6 | $R^{1b}$-1 | I |
| A-6 | $R^{1b}$-1 | OH |
| A-6 | $R^{1b}$-1 | OAc |
| A-6 | $R^{1b}$-1 | OTf |
| A-6 | $R^{1b}$-1 | OPh |
| A-6 | $R^{1b}$-1 | BF$_4$ |
| A-6 | $R^{1b}$-1 | PF$_6$ |
| A-6 | $R^{1b}$-1 | PS—SO$_3$ |
| A-7 | CH=CH$_2$ | Br |
| A-7 | CH=CH$_2$ | Cl |
| A-7 | CH=CH$_2$ | I |
| A-7 | CH=CH$_2$ | OH |
| A-7 | CH=CH$_2$ | OAc |
| A-7 | CH=CH$_2$ | OTf |
| A-7 | CH=CH$_2$ | OPh |
| A-7 | CH=CH$_2$ | BF$_4$ |
| A-7 | CH=CH$_2$ | PF$_6$ |
| A-7 | CH=CH$_2$ | PS—SO$_3$ |
| A-7 | CH$_2$—CH$_3$ | Br |
| A-7 | CH$_2$—CH$_3$ | Cl |
| A-7 | CH$_2$—CH$_3$ | I |
| A-7 | CH$_2$—CH$_3$ | OH |
| A-7 | CH$_2$—CH$_3$ | OAc |
| A-7 | CH$_2$—CH$_3$ | OTf |
| A-7 | CH$_2$—CH$_3$ | OPh |
| A-7 | CH$_2$—CH$_3$ | BF$_4$ |
| A-7 | CH$_2$—CH$_3$ | PF$_6$ |
| A-7 | CH$_2$—CH$_3$ | PS—SO$_3$ |
| A-7 | $R^{1b}$-1 | Br |
| A-7 | $R^{1b}$-1 | Cl |
| A-7 | $R^{1b}$-1 | I |
| A-7 | $R^{1b}$-1 | OH |
| A-7 | $R^{1b}$-1 | OAc |
| A-7 | $R^{1b}$-1 | OTf |
| A-7 | $R^{1b}$-1 | OPh |
| A-7 | $R^{1b}$-1 | BF$_4$ |
| A-7 | $R^{1b}$-1 | PF$_6$ |
| A-7 | $R^{1b}$-1 | PS—SO$_3$ |
| A-8 | CH=CH$_2$ | Br |
| A-8 | CH=CH$_2$ | Cl |
| A-8 | CH=CH$_2$ | I |

-continued

| A | $R^{1b}$ | $X^{1b}$ |
|---|---|---|
| A-8 | $CH=CH_2$ | OH |
| A-8 | $CH=CH_2$ | OAc |
| A-8 | $CH=CH_2$ | OTf |
| A-8 | $CH=CH_2$ | OPh |
| A-8 | $CH=CH_2$ | $BF_4$ |
| A-8 | $CH=CH_2$ | $PF_6$ |
| A-8 | $CH=CH_2$ | $PS-SO_3$ |
| A-8 | $CH_2-CH_3$ | Br |
| A-8 | $CH_2-CH_3$ | Cl |
| A-8 | $CH_2-CH_3$ | I |
| A-8 | $CH_2-CH_3$ | OH |
| A-8 | $CH_2-CH_3$ | OAc |
| A-8 | $CH_2-CH_3$ | OTf |
| A-8 | $CH_2-CH_3$ | OPh |
| A-8 | $CH_2-CH_3$ | $BF_4$ |
| A-8 | $CH_2-CH_3$ | $PF_6$ |
| A-8 | $CH_2-CH_3$ | $PS-SO_3$ |
| A-8 | $R^{1b}$-1 | Br |
| A-8 | $R^{1b}$-1 | Cl |
| A-8 | $R^{1b}$-1 | I |
| A-8 | $R^{1b}$-1 | OH |
| A-8 | $R^{1b}$-1 | OAc |
| A-8 | $R^{1b}$-1 | OTf |
| A-8 | $R^{1b}$-1 | OPh |
| A-8 | $R^{1b}$-1 | $BF_4$ |
| A-8 | $R^{1b}$-1 | $PF_6$ |
| A-8 | $R^{1b}$-1 | $PS-SO_3$ |

The amount of the phase transfer catalyst is usually 0.0001 mol to 10 mol, preferably 0.0005 mol to 1 mol, and particularly preferably 0.001 mol to 0.5 mol for 1 mol of an α,β-unsaturated carbonyl compound.

Examples of a base that can be used in a reaction of the present invention include sodium hydroxide, potassium hydroxide, barium hydroxide, lithium hydroxide, potassium phosphate, sodium phosphate, sodium acetate, sodium methoxide, potassium-t-butoxide, pyridine, piperidine, and triethylamine; and sodium hydroxide or potassium hydroxide is preferable.

Although water is usually added in a reaction of the present invention, the reaction can be conducted without water.

A reaction according to the present invention can be conducted, for example, by placing the given amounts of an α,β-unsaturated carbonyl compound of Formula (1), a chiral phase transfer catalyst, and a solvent such as methylene chloride in a reactor; dropping a solution containing a base, water, and hydroxylamine into the reactor usually at −70° C. to 100° C., preferably at −40° C. to 50° C. with stirring; and reacting usually for 10 minutes to 120 hours, preferably for 1 hour to 48 hours.

Among compounds of Formula (1) used herein, some are known compounds, and can be synthesized, for example, according to a method described in WO 2009/063910 and a general method described in a literature relating to a known compound.

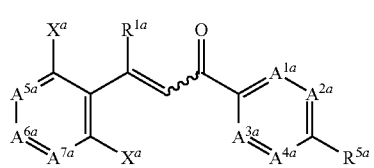
(1)

A method for synthesizing compounds of Formulae (2) to (5) will be explained below.

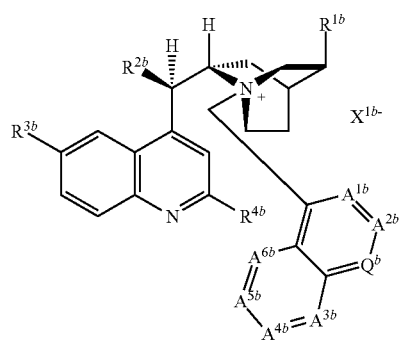
(2)

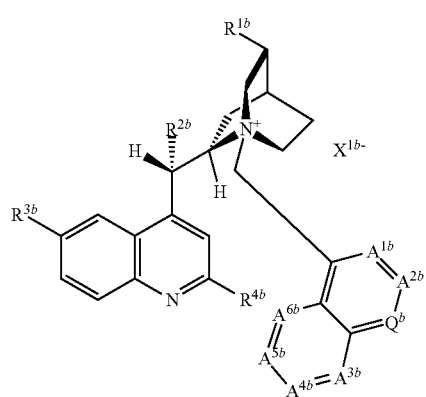
(3)

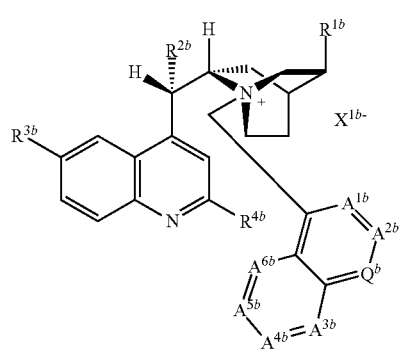
(4)

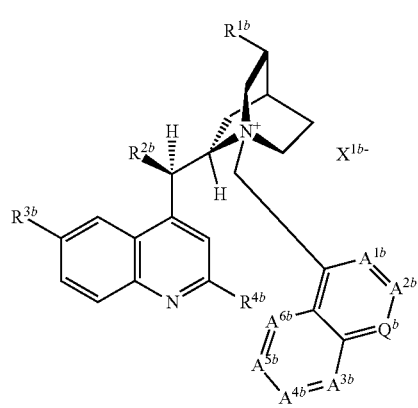
(5)

Compounds of Formulae (2) to (5) can be synthesized according to a known method described in a known literature, for example, European Journal of Organic Chemistry, 2002, Volume 13, Page 2087. As an example, a method for synthesizing a compound of Formula (2) will be explained in detail below.

Specifically, by allowing a compound of Formula (14) [in the formula, each of, $R^{1b}$, $R^{2b}$, $R^{3b}$ and $R^{4b}$ is same as that described above] to react with a halide compound of Formula (16) [in the formula, each of $A^{1b}$, $A^{2b}$, $A^{3b}$, $A^{4b}$, $A^{5b}$, $A^{6b}$ and $Q^b$ is same as that described above, and $X^{2b}$ is a bromine atom or a chlorine atom] in the presence of a base, a compound of Formula (2-1) [in the formula, each of $R^{1b}$, $R^{2b}$, $R^{3b}$, $R^{4b}$, $A^{1b}$, $A^{2b}$, $A^{3b}$, $A^{4b}$, $A^{5b}$, $A^{6b}$, and $Q^b$ is same as that described above, and $X^{2b}$ is a bromine atom or a chlorine atom] can be obtained.

Production Method 1

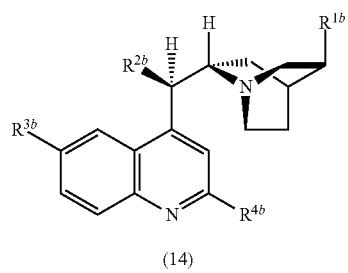

(14)

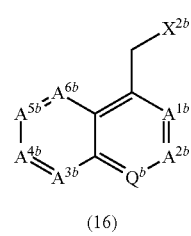

(16)

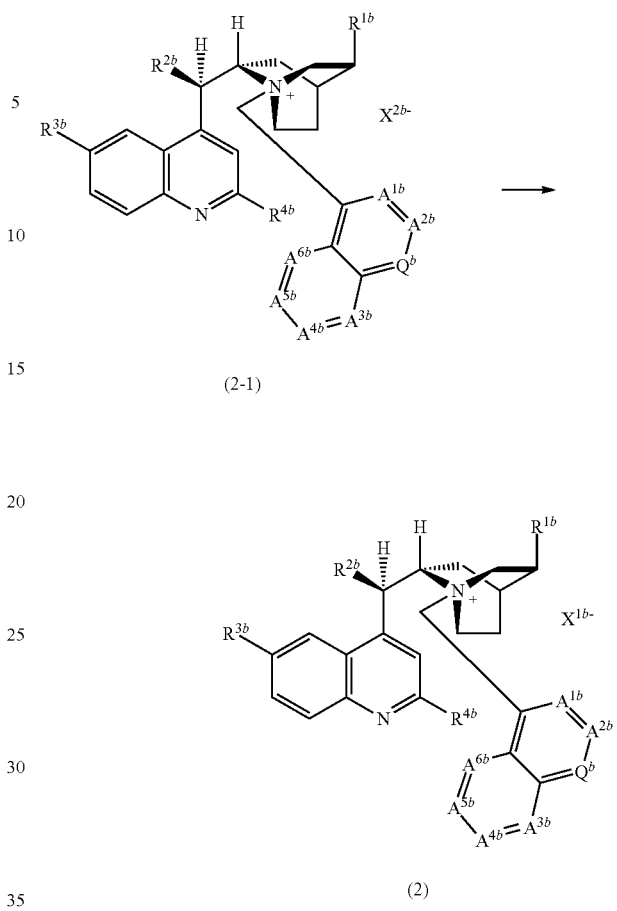

(2-1)

(2)

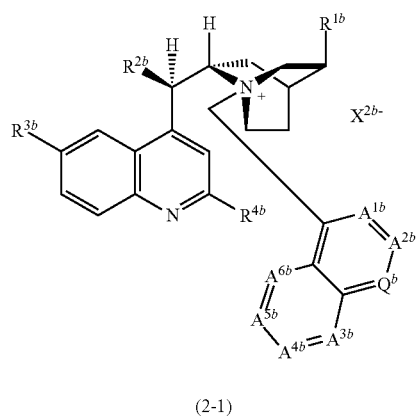

(2-1)

Moreover, by subjecting a compound of Formula (2-1) to an ion exchange reaction, a compound of Formula (2) [in the formula, each of $R^{1b}$, $R^{2b}$, $R^{3b}$, $R^{4b}$, $A^{1b}$, $A^{2b}$, $A^{3b}$, $A^{4b}$, $A^{5b}$, $A^{6b}$, $Q^b$ and $X^{1b}$ is same as that described above] can be obtained. The ion exchange reaction can be conducted by, for example, allowing a silver salt $AgX^{1b}$ to react with a compound of Formula (2-1).

Among compounds of Formula (14) used in Production Method 1, some are known compounds, and may be commercially available. Other compounds can be synthesized according to a known synthetic method described in a known literature, for example, Synthesis Example 1.

Synthesis Example 1

Known cinchona alkaloid compounds (13), for example, cinchonine, cinchonidine, quinine, quinidine, hydrocinchonine, hydrocinchonidine, hydroquinine, hydroquinidine, (8α, 9S)-6'-methoxy cinchonan-9-amine, quinine-9-epiamine, and dihydroquinine-9-epiamine were used as starting raw materials. For $R^{1b}$, examples include forming an isoxazoline ring by using the 1,3-dipolar cycloaddition reaction that is a converting method of terminal olefin, forming epoxide by an epoxidized reaction, and an introducing an aromatic ring in olefin by Mizoroki-Heck reaction. For $R^{2b}$, examples include esterification, amidation, and etherification. For $R^{3b}$, examples include converting a methoxy group to another alkoxy group. For $R^{4b}$, examples include conversion for introducing an aromatic ring (see, for example, Cinchona Alkaloids in Synthesis and Catalysis: Ligands, Immobilization and Organocatalysis, 2009, Wiley-VCH and Journal of the American Chemical Society, 2010, Volume 132, Page 13194).

Synthesis Example 1
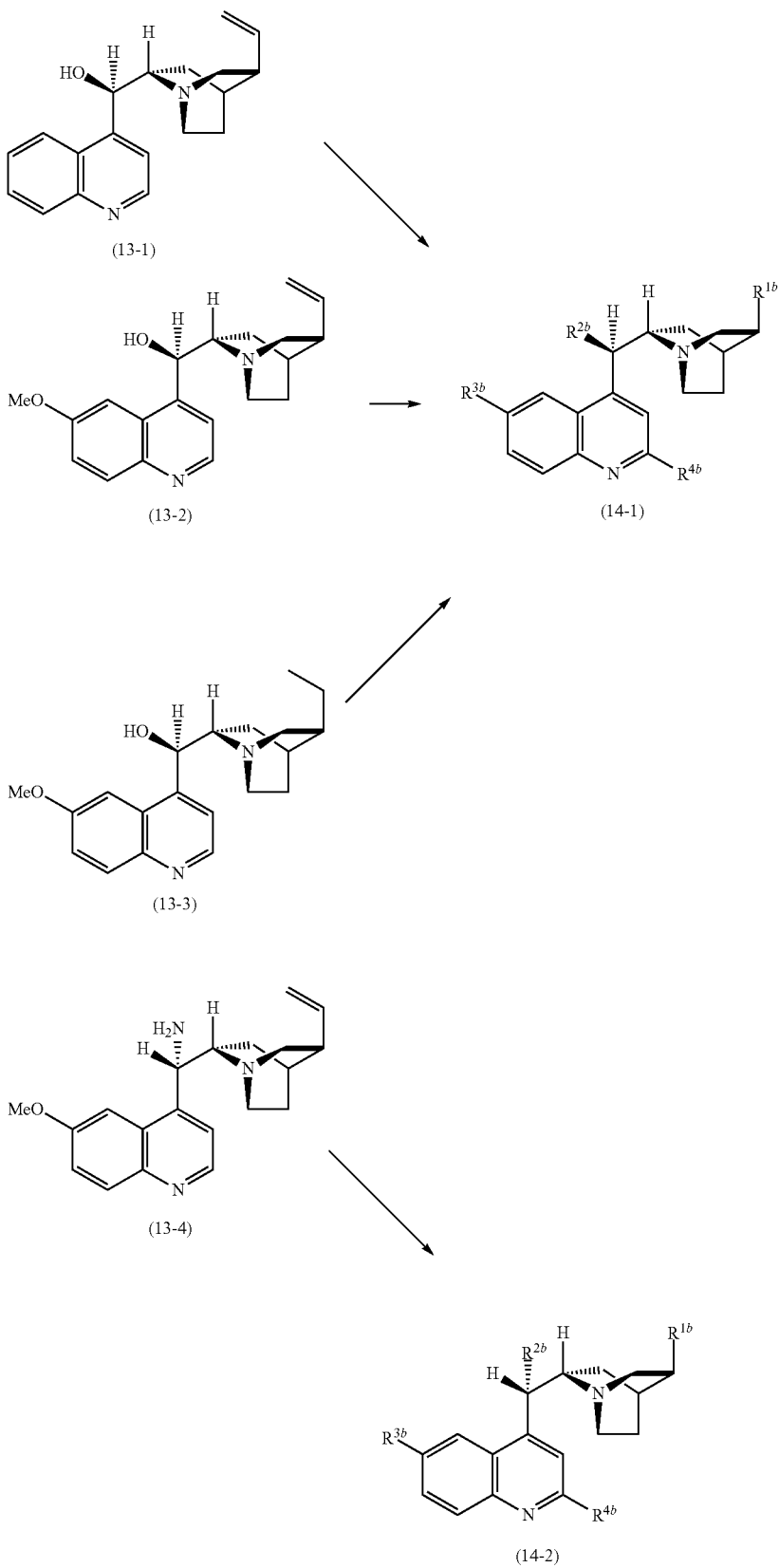

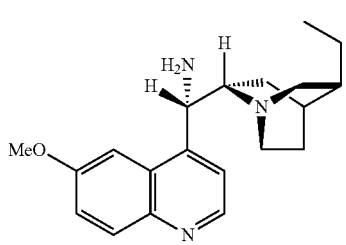

(13-5)

Among compounds of Formula (16) used in Production Method 1, some are known compounds, and may be commercially available. Other compounds can be synthesized according to a known synthetic method described in a known literature, for example, Synthesis Example 2.

Synthesis Example 2

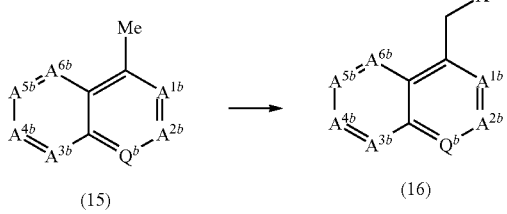

By allowing a compound of known Formula (15) [in the formula, each of $A^{1b}$, $A^{2b}$, $A^{3b}$, $A^{4b}$, $A^{5b}$, $A^{6b}$, and $Q^b$ is same as that described above] to react with a brominating agent such as N-bromosuccinimide or a chlorinating agent such as N-chlorosuccinimide, a compound of Formula (16) [in the formula, $A^{1b}$, $A^{2b}$, $A^{3b}$, $A^{4b}$, $A^{5b}$, $A^{6b}$ and $Q^b$ is same as that described above, and $X^{2b}$ is a bromine atom or a chlorine atom] can be obtained.

Among compounds of Formula (16) used in Production Method 1, some are compounds of Formula (16-1), that is, 9-halomethyl-substituted acridine compounds, and can be synthesized according to, for example, Synthesis Example 3.

Synthesis Example 3

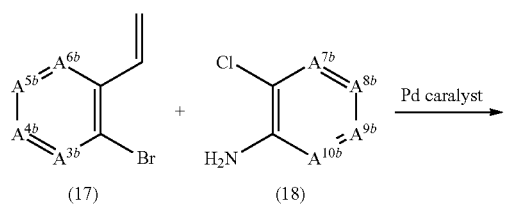

By allowing a compound of known Formula (17) [in the formula, each of $A^{3b}$, $A^{4b}$, $A^{5b}$, and $A^{6b}$ is same as that described above] to react with a compound of Formula (18) [in the formula, $A^{7b}$, $A^{8b}$, $A^{9b}$, and $A^{10b}$ is same as that described above] in the presence of an appropriate Pd catalyst, a compound of Formula (19) [in the formula, each of $A^{3b}$, $A^{4b}$, $A^{5b}$, $A^{6b}$, $A^{7b}$, $A^{8b}$, $A^{9b}$, and $A^{10b}$ is same as that described above] can be synthesized. Then, a compound of Formula (15-1) [in the formula, each of $A^{3b}$, $A^{4b}$, $A^{5b}$, $A^{6b}$, $A^{7b}$, $A^{8b}$, $A^{9b}$, and $A^{10b}$ is same as that described above] is synthesized by using another appropriate Pd catalyst, and by allowing the compound of Formula (15-1) to react with a brominating agent such as N-bromosuccinimide or a chlorinating agent such as N-chlorosuccinimide, a compound of Formula (16-1) [in the formula, each of $A^{3b}$, $A^{4b}$, $A^{5b}$, $A^{6b}$, $A^{7b}$, $A^{8b}$, $A^{9b}$, and $A^{10b}$ is same as that described above, and $X^{2b}$ is a bromine atom or a chlorine atom] can be synthesized. A chiral phase transfer catalyst having substituted acridine can be synthesized from these compounds according to the method described above (see, for example, Journal of the American Chemical Society, 2010, Volume 132, Page 14048).

Examples

Hereinafter, examples of the present invention will be described; however, the present invention is not limited thereto.

Example 1

(S)-4-(5-(3,5-dichlorophenyl)-5-trifluoromethyl-4,5-dihydroisoxazol-3-yl)-2-methyl benzamide 101 mg (0.25 mmol) of 4-(3-(3,5-dichlorophenyl)-4,4,4-trifluoro-2-butenoyl)-2-methyl benzamide (E isomer/Z isomer=99.9/0.1) was dissolved in 3 mL of methylene chloride, then 30 mg (0.05 mmol) of N-(acridin-9-ylmethyl)quininium bromide was added, and stirred at −20° C. To the solution, a solution separately prepared by mixing 0.055 mL (0.55 mmol) of 10 N sodium hydroxide aqueous solution, 0.0425 mL of purified water, and 0.0275 mL (0.50 mmol) of 50% hydroxylamine aqueous solution, was dropped.

A few drops of the reaction solution was added to 0.5 mL of purified water, and diluted with acetonitrile to 1.5 mL to analyze with high performance liquid chromatography (the conditions of analysis were as follows: column: Zorbax eclipse XDB-C8, 5 μm, 4.6×150 mm, eluent: acetonitrile/0.1% formic acid aqueous solution=3/1, flow rate: 1.0 mL/minute, oven temperature: 45° C., and detection: a UV detector with a wavelength of 254 nm). An analysis with high performance liquid chromatography showed that an area percentage of 4-(5-(3,5-dichlorophenyl)-5-trifluoromethyl-4,5-dihydroisoxazol-3-yl)-2-methylbenzamide after 20 hours was 96.9%.

After the conversion rate was confirmed, the reaction solution was charged in 2 g/12 mL of a solid-phase extraction column Mega Bond Elut SI (manufactured by Varian, Inc), run with 30 mL of hexane/ethyl acetate=1/1 (v/v), and the solvent was removed from the extract by distillation. The extract was analyzed with high performance liquid chromatography equipped with a chiral HPLC column, and it was confirmed that the retention time of each of the enantiomers was 5.70 minutes/7.06 minutes=96.8/3.2 (the conditions of analysis were as follows: chiral HPLC column: Chiralpak AD-3, 3 μm, 2.1×250 mm, eluent: hexane/ethanol=9/1, flow rate: 0.6 mL/minute, oven temperature: 30° C., and detection: a UV detector with a wavelength of 254 nm).

Comparative Example 1

101 mg (0.25 mmol) of 4-(3-(3,5-dichlorophenyl)-4,4,4-trifluoro-2-butenoyl)-2-methyl benzamide (E isomer/Z isomer=99.9/0.1) was dissolved in 3 mL of methylene chloride, then 27.5 mg (0.05 mmol) of N-(anthracenyl methyl)quininium bromide was added, and stirred at −20° C. To the solution, a solution separately prepared by mixing 0.055 mL (0.55 mmol) of 10 N sodium hydroxide aqueous solution, 0.0425 mL of purified water, and 0.0275 mL (0.50 mmol) of 50% hydroxylamine aqueous solution, was dropped.

A few drops of the reaction solution was added to 0.5 mL of purified water, and diluted with acetonitrile to 1.5 mL to analyze with high performance liquid chromatography (the conditions of analysis were as follows: column: Zorbax eclipse XDB-C8, 5 μm, 4.6×150 mm, eluent: acetonitrile/0.1% formic acid aqueous solution=3/1, flow rate: 1.0 mL/minute, oven temperature: 45° C., and detection: a UV detector with a wavelength of 254 nm). An analysis with high performance liquid chromatography showed that an area percentage of 4-(5-(3,5-dichlorophenyl)-5-trifluoromethyl-4,5-dihydroisoxazol-3-yl)-2-methylbenzamide after 20 hours was 96.0%.

After the conversion rate was confirmed, the reaction solution was charged in 2 g/12 mL of a solid-phase extraction column Mega Bond Elut SI (manufactured by Varian, Inc.), run with 30 mL of hexane/ethyl acetate=1/1 (v/v), and the solvent was removed from the extract by distillation. The extract was analyzed with high performance liquid chromatography equipped with a chiral HPLC column, and it was confirmed that the retention time of each of the enantiomers was 5.70 minutes/7.06 minutes=77.7/22.3 (the conditions of analysis were as follows: chiral HPLC column: Chiralpak AD-3, 3 μm, 2.1×250 mm, eluent: hexane/ethanol=9/1, flow rate: 0.6 mL/minute, oven temperature: 30° C., and detection: a UV detector with a wavelength of 254 nm).

Example 2

(S)-4-(5-(3,5-dichlorophenyl)-5-trifluoromethyl-4,5-dihydroisoxazol-3-yl)-2-methyl-N-(2-oxo-2-(2,2,2-trifluoroethylamino)ethyl)benzamide 100 mg (0.18 mmol) of 4-(3-(3,5-dichlorophenyl)-4,4,4-trifluoro-2-butenoyl)-2-methyl-N-(2-oxo-2-(2,2,2-trifluoroethylamino)ethyl)benzamide was dissolved in 2.2 mL of methylene chloride, then 22 mg (0.037 mmol) of N-(acridin-9-ylmethyl)quininium bromide was added, and stirred at −20° C. To the solution, a solution separately prepared by mixing 0.041 mL (0.41 mmol) of 10 N sodium hydroxide aqueous solution, 0.031 mL of purified water, and 0.021 mL (0.37 mmol) of 50% hydroxylamine aqueous solution, was dropped.

A few drops of the reaction solution was added to 0.5 mL of purified water, and diluted with acetonitrile to 1.5 mL to analyze with high performance liquid chromatography (the conditions of analysis were as follows: column: Zorbax eclipse XDB-C8, 5 μm, 4.6×150 mm, eluent: acetonitrile/0.1% formic acid aqueous solution=3/1, flow rate: 1.0 mL/minute, oven temperature: 45° C., and detection: a UV detector with a wavelength of 254 nm). An analysis with high performance liquid chromatography showed that an area percentage of 4-(5-(3,5-dichlorophenyl)-5-trifluoromethyl-4,5-dihydroisoxazol-3-yl)-2-methyl-N-(2-oxo-2-(2,2,2-trifluoroethylamino)ethyl)benzamide after 20 hours was 94.3%.

After the conversion rate was confirmed, the reaction solution was charged in 2 g/12 mL of a solid-phase extraction column Mega Bond Elut SI (manufactured by Varian, Inc), run with 30 mL of hexane/ethyl acetate=1/1 (v/v), and the solvent was removed from the extract by distillation. The extract was analyzed with high performance liquid chromatography equipped with a chiral HPLC column, and it was confirmed that the retention time of each of the enantiomers was 8.85 minutes/23.65 minutes=96.3/3.7 (the conditions of analysis were as follows: chiral HPLC column: Chiralpak AD-3, 3 μm, 2.1×250 mm, eluent: hexane/ethanol=9/1, flow rate: 0.6 mL/minute, oven temperature: 30° C., and detection: a UV detector with a wavelength of 254 nm).

Comparative Example 2

133 mg (0.25 mmol) of 4-(3-(3,5-dichlorophenyl)-4,4,4-trifluoro-2-butenoyl)-2-methyl-N-(2-oxo-2-(2,2,2-trifluoroethylamino)ethyl)benzamide was dissolved in 3.1 mL of 1,2-dichloroethane, then 39.1 mg (0.075 mmol) of N-(anthracenyl methyl)cinchonidinium chloride was added, and stirred at −20° C. To the solution, a solution separately prepared by mixing 0.055 mL (0.55 mmol) of 10 N sodium hydroxide aqueous solution, 0.060 mL of purified water, and 0.0275 mL (0.50 mmol) of 50% hydroxylamine aqueous solution, was dropped.

A few drops of the reaction solution was added to 0.5 mL of purified water, and diluted with acetonitrile to 1.5 mL to analyze with high performance liquid chromatography (the conditions of analysis were as follows: column: Zorbax eclipse XDB-C8, 5 μm, 4.6×150 mm, eluent: acetonitrile/0.1%-formic acid aqueous solution=3/1, flow rate: 1.0 mL/minute, oven temperature: 45° C., and detection: a UV detector with a wavelength of 254 nm). An analysis with high performance liquid chromatography showed that an area percentage of 4-(5-(3,5-dichlorophenyl)-5-trifluoromethyl-4,5-dihydroisoxazol-3-yl)-2-methyl-N-(2-oxo-2-(2,2,2-trifluoroethylamino)ethyl)benzamide after 20 hours was 92.1%.

After the conversion rate was confirmed, the reaction solution was charged in 2 g/12 mL of a solid-phase extraction column Mega Bond Elut SI (manufactured by Varian, Inc), run with 30 mL of hexane/ethyl acetate=1/1 (v/v), and the solvent was removed from the extract by distillation. The extract was analyzed with high performance liquid chromatography equipped with a chiral HPLC column, and it was confirmed that the retention time of each of the enantiomers was 8.85 minutes/23.65 minutes=56.5/43.5 (the conditions of analysis were as follows: chiral HPLC column: Chiralpak AD-3, 3 μm, 2.1×250 mm, eluent: hexane/ethanol=9/1, flow rate: 0.6 mL/minute, oven temperature: 30° C., and detection: a UV detector with a wavelength of 254 nm).

Example 3

(S)-4-(5-(3,5-dichlorophenyl)-5-trifluoromethyl-4,5-dihydroisoxazol-3-yl)-2-methyl-N-(2-ethyl-3-oxo-isoxazolidine-4-yl)benzamide 83 mg (0.16 mmol) of 4-(3-(3,5-dichlorophenyl)-4,4,4-trifluoro-2-butenoyl)-N-(2-ethyl-3-oxo-isoxazolidine-4-yl)-2-methylbenzamide was dissolved in 2 mL of methylene chloride, then 19 mg (0.03 mmol) of N-(acridin-9-ylmethyl)quininium bromide was added, and stirred at −20° C. To the solution, a solution separately prepared by mixing 0.035 mL (0.35 mmol) of 10 N sodium hydroxide aqueous solution, 0.027 mL of purified water, and 0.018 mL (0.32 mmol) of 50% hydroxylamine aqueous solution, was dropped.

A few drops of the reaction solution was added to 0.5 mL of purified water, and diluted with acetonitrile to 1.5 mL to analyze with high performance liquid chromatography (the conditions of analysis were as follows: column: Zorbax eclipse XDB-C8, 5 μm, 4.6×150 mm, eluent: acetonitrile/0.1% formic acid aqueous solution=3/1, flow rate: 1.0 mL/minute, oven temperature: 45° C., and detection: a UV detector with a wavelength of 254 nm). An analysis with high performance liquid chromatography showed that an area percentage of 4-(5-(3,5-dichlorophenyl)-5-trifluoromethyl-4,5-dihydroisoxazol-3-yl)-2-methylbenzamide after 20 hours was 93.4%.

After the conversion rate was confirmed, the reaction solution was charged in 2 g/12 mL of a solid-phase extraction column Mega Bond Elut SI (manufactured by Varian, Inc), run with 30 mL of hexane/ethyl acetate=1/1 (v/v), and the solvent was removed from the extract by distillation. The extract was analyzed with high performance liquid chromatography equipped with a chiral HPLC column, and it was confirmed that the retention time of each of the diastereomers was 17.98 minutes/26.38 minutes/32.25 minutes/49.70 minutes=6.41/89.61/0.34/3.64 (the conditions of analysis were as follows: Chiral HPLC column: Chiralpak AD-3, 3 μm, 2.1×250 mm, eluent: hexane/ethanol=9/1, flow rate: 0.6 mL/minute, oven temperature: 30° C., and detection: a UV detector with a wavelength of 254 nm).

Comparative Example 3

Step B of Example 37 described in WO 2011/067272 is used as Comparative Example 3.

Example 4

(S)—N-(4-(5-(3-bromo-5-trifluoromethylphenyl)-5-trifluoromethyl-4,5-dihydroisoxazol-3-yl)-2-chlorobenzyl)butylamide 112 mg (0.20 mmol) of N-(4-(3-(3-bromo-5-trifluoromethylphenyl)-4,4,4-trifluoro-2-butenoyl)-2-chlorobenzyl)butylamide was dissolved in 2.4 mL of methylene chloride, then 24 mg (0.04 mmol) of N-(acridin-9-ylmethyl)quininium bromide was added, and stirred at −20° C. To the solution, a solution separately prepared by mixing 0.044 mL (0.44 mmol) of 10 N sodium hydroxide aqueous solution, 0.034 mL of purified water, and 0.022 mL (0.40 mmol) of 50% hydroxylamine aqueous solution, was dropped.

A few drops of the reaction solution was added to 0.5 mL of purified water, and diluted with acetonitrile to 1.5 mL to analyze with high performance liquid chromatography (the conditions of analysis were as follows: column: Zorbax eclipse XDB-C8, 5 μm, 4.6×150 mm, eluent: acetonitrile/0.1% formic acid aqueous solution=3/1, flow rate: 1.0 mL/minute, oven temperature: 45° C., and detection: a UV detector with a wavelength of 254 nm). An analysis with high performance liquid chromatography showed that an area percentage of N-(4-(5-(3-bromo-5-trifluoromethylphenyl)-5-trifluoromethyl-4,5-dihydroisoxazol-3-yl)-2-chlorobenzyl)butylamide after 20 hours was 100%.

After the conversion rate was confirmed, the reaction solution was charged in 2 g/12 mL of a solid-phase extraction column Mega Bond Elut SI (manufactured by Varian, Inc), run with 30 mL of hexane/ethyl acetate=1/1 (v/v), and the solvent was removed from the extract by distillation. The extract was analyzed with high performance liquid chromatography equipped with a chiral HPLC column, and it was confirmed that the retention time of each of the enantiomers was 2.44 minutes/4.63 minutes=84.0/16.0 (the conditions of analysis were as follows: chiral HPLC column: Chiralpak AD-3, 3 μm, 2.1×250 mm, eluent: hexane/ethanol=9/1, flow rate: 0.6 mL/minute, oven temperature: 30° C., and detection: a UV detector with a wavelength of 254 nm).

Comparative Example 4

112 mg (0.20 mmol) of N-(4-(3-(3-bromo-5-trifluoromethylphenyl)-4,4,4-trifluoro-2-butenoyl)-2-chlorobenzyl)butylamide was dissolved in 2.4 mL of methylene chloride, then 22 mg (0.04 mmol) of N-(anthracenyl methyl)quininium bromide was added, and stirred at −20° C. To the solution, a solution separately prepared by mixing 0.044 mL (0.44 mmol) of 10 N sodium hydroxide aqueous solution, 0.034 mL of purified water, and 0.022 mL (0.40 mmol) of 50% hydroxylamine aqueous solution, was dropped.

A few drops of the reaction solution was added to 0.5 mL of purified water, and diluted with acetonitrile to 1.5 mL to analyze with high performance liquid chromatography (the conditions of analysis were as follows: column: Zorbax eclipse XDB-C8, 5 μm, 4.6×150 mm, eluent: acetonitrile/

0.1% formic acid aqueous solution=3/1, flow rate: 1.0 mL/minute, oven temperature: 45° C., and detection: a UV detector with a wavelength of 254 nm). An analysis with high performance liquid chromatography showed that an area percentage of N-(4-(5-(3-bromo-5-trifluoromethylphenyl)-5-trifluoromethyl-4,5-dihydroisoxazol-3-yl)-2-chlorobenzyl) butylamide after 20 hours was 90.7%.

After the conversion rate was confirmed, the reaction solution was charged in 2 g/12 mL of a solid-phase extraction column Mega Bond Elut SI (manufactured by Varian, Inc), run with 30 mL of hexane/ethyl acetate=1/1 (v/v), and the solvent was removed from the extract by distillation. The extract was analyzed with high performance liquid chromatography equipped with a chiral HPLC column, and it was confirmed that the retention time of each of the enantiomers was 2.44 minutes/4.63 minutes=68.9/31.1 (the conditions of analysis were as follows: chiral HPLC column: Chiralpak AD-3, 3 μm, 2.1×250 mm, eluent: hexane/ethanol=9/1, flow rate: 0.6 mL/minute, oven temperature: 30° C., and detection: a UV detector with a wavelength of 254 nm).

The conditions of reactions and results obtained in Examples 1 to 4 and Comparative Examples 1 to 4 are listed in Table 2 below.

TABLE 2

| | α,β-Unsaturated Carbonyl Compounds: I | (4,5-dihydroisoxazol-3-yl)aryl Compounds: II | PTC | Chiral Temperature (°C.) | Area Percentage of II (%) | Enantiomeric Ratio S | Enantiomeric Ratio R | ee % |
|---|---|---|---|---|---|---|---|---|
| Example 1 | (structure) | (structure) | A | −20 | 96.9 | 96.8 | 3.2 | 93.6 |
| Comparative Example 1 | | | B-1 | −20 | 96.0 | 77.7 | 22.3 | 55.4 |
| Example 2 | (structure) | (structure) | A | −20 | 94.3 | 96.3 | 3.7 | 92.6 |
| Comparative Example 2 | | | B-2 | −20 | 92.1 | 56.5 | 43.5 | 13.0 |
| Example 3 | (structure) | (structure) | A | −20 | 93.4 | 96.0 | 4.0 | 92.0 |
| Comparative Example 3 | | | B-1 | 0 | — | 66.7 | 33.3 | 33.4 |

TABLE 2-continued (4,5-dihydroisoxazol-3-yl)aryl Compounds: II

| | α,β-Unsaturated Carbonyl Compounds: I | Compounds: II | Chiral PTC | Temperature (°C.) | Area Percentage of II (%) | Enantiomeric Ratio S | R | ee % |
|---|---|---|---|---|---|---|---|---|
| Example 4 | | | A | -20 | 100 | 84.0 | 16.0 | 68.0 |
| Comparative Example 4 | | | B-1 | -20 | 90.7 | 68.9 | 31.1 | 37.8 |

(Annotation 1) Chiral PTC* (PTC=an abbreviation of phase transfer catalyst, the same applies hereinafter)
A: N-(acridin-9-ylmethyl)quininium bromide
B-1: N-(anthracenylmethyl)quininium bromide
B-2: N-(anthracenylmethyl)cinchonidinium chloride
(Annotation 2)
How absolute configurations were determined will be explained below.

For Examples 1 to 3, the description in Japanese Patent Application Publication No. 2011-051977, which explains that an absolute configuration of (S)-4-(5-(3,5-dichlorophenyl)-5-trifluoromethyl-4,5-dihydroisoxazol-3-yl)-2-methylbenzoic acid was determined with X-ray crystallography, was applied to each of the induced compounds II to determine an absolute configuration.

For Example 4, a single crystal X-ray structural analysis was conducted to determine an absolute configuration of the compounds II itself.

Example 5

In a reaction vessel, 12 mL of methylene chloride, 119 mg (0.2 mmol) of N-(acridin-9-ylmethyl)quininium bromide, 0.22 mL (2.2 mmol) of 10 N sodium hydroxide aqueous solution, 0.17 mL of purified water, and 0.11 mL (2.0 mmol) of 50% hydroxylamine aqueous solution were mixed, and stirred at −20° C. To the mixture, 402 mg (1.0 mmol) of 4-(3-(3,5-dichlorophenyl)-4,4,4-trifluoro-2-butenoyl)-2-methyl benzamide (E isomer/Z isomer=99.9/0.1) was charged in fractional amounts (20 to 30 mg/1 charge) over 5 hours.

A few drops of the reaction solution was added to 0.5 mL of purified water, and diluted with acetonitrile to 1.5 mL to analyze with high performance liquid chromatography (the conditions of analysis were as follows: column: Zorbax eclipse XDB-C8, 5 μm, 4.6×150 mm, eluent: acetonitrile/0.1% formic acid aqueous solution=3/1, flow rate: 1.0 mL/minute, oven temperature: 45° C., and detection: a UV detector with a wavelength of 254 nm). An analysis with high performance liquid chromatography showed that an area percentage of 4-(5-(3,5-dichlorophenyl)-5-trifluoromethyl-4,5-dihydroisoxazol-3-yl)-2-methyl benzamide after 20 hours was 94.1%.

After the conversion rate was confirmed, the reaction solution was charged in 2 g/12 mL of a solid-phase extraction column Mega Bond Elut SI (manufactured by Varian, Inc), run with 30 mL of hexane/ethyl acetate=1/1 (v/v), and the solvent was removed from the extract by distillation. The extract was analyzed with high performance liquid chromatography equipped with a chiral HPLC column, and it was confirmed that the retention time of each of the enantiomers was 5.70 minutes/7.06 minutes=97.3/2.7 (the conditions of analysis were as follows: chiral HPLC column: Chiralpak AD-3, 3 μm, 2.1×250 mm, eluent: hexane/ethanol=9/1, flow rate: 0.6 mL/minute, oven temperature: 30° C., and detection: a UV detector with a wavelength of 254 nm).

To the solid, 2 mL of diisopropyl ether and 4 mL of hexane were added, and stirred. The solvent was removed by filtration, and remaining was dried under reduced pressure to obtain 304 mg of a solid. An analysis with the high performance liquid chromatography equipped with a chiral HPLC column described above showed that any peaks indicating R isomers were not observed, and enantiomeric excess of S isomers was 99% ee or above. From the result of $^1$H-NMR, the obtained solid seemed to be a 2:1 solvate of (S)-4-(5-(3,5-dichlorophenyl)-5-trifluoromethyl-4,5-dihydroisoxazol-3-yl)-2-methyl benzamide and diisopropyl ether.

$^1$H NMR (CDCl$_3$, Me$_4$Si, 300 MHz) δ 7.45-7.60 (m, 5H), 7.43 (s, 1H), 6.02 (brs, 1H), 5.86 (brs, 1H), 4.09 (d, J=17.4 Hz, 1H), 3.70 (d, J=17.4 Hz, 1H), 3.55-3.75 (m, 1H), 2.51 (s, 3H), 1.13 (d, J=6.0 Hz, 6H).

Melting point: 148-151° C.

Example 6

101 mg (0.25 mmol) of 4-(3-(3,5-dichlorophenyl)-4,4,4-trifluoro-2-butenoyl)-2-methyl benzamide (E isomer/Z isomer=99.9/0.1) was dissolved in 3 mL of methylene chloride, then 30 mg (0.05 mmol) of N-(acridin-9-ylmethyl)quininium bromide was added, and stirred at 0° C. To the solution, a solution separately prepared by mixing 0.055 mL (0.55 mmol) of 10 N sodium hydroxide aqueous solution, 0.0425 mL of purified water, and 0.0275 mL (0.50 mmol) of 50% hydroxylamine aqueous-solution, was dropped.

A few drops of the reaction solution was added to 0.5 mL of purified water, and diluted with acetonitrile to 1.5 mL to analyze with high performance liquid chromatography (the conditions of analysis were as follows: column: Zorbax eclipse XDB-C8, 5 μm, 4.6×150 mm, eluent: acetonitrile/0.1% formic acid aqueous solution=3/1, flow rate: 1.0 mL/minute, oven temperature: 45° C., and detection: a UV detector with a wavelength of 254 nm). An analysis with high performance liquid chromatography showed that an area percentage of 4-(5-(3,5-dichlorophenyl)-5-trifluoromethyl-4,5-dihydroisoxazol-3-yl)-2-methylbenzamide after 3 hours was 100%.

After the conversion rate was confirmed, the reaction solution was charged in 2 g/12 mL of a solid-phase extraction column Mega Bond Elut SI (manufactured by Varian, Inc), run with 30 mL of hexane/ethyl acetate=1/1 (v/v), and the solvent was removed from the extract by distillation. The extract was analyzed with high performance liquid chromatography equipped with a chiral HPLC column, and it was confirmed that the retention time of each of the enantiomers was 5.70 minutes/7.06 minutes=95.2/4.8 (the conditions of analysis were as follows: chiral HPLC column: Chiralpak AD-3, 3 μm, 2.1×250 mm, eluent: hexane/ethanol=9/1, flow rate: 0.6 mL/minute, oven temperature: 30° C., and detection: a UV detector with a wavelength of 254 nm).

Example 7

Preparation of PTC: 2-methoxy-4-methyl quinoline quininium bromide

Step 1

1.0 g (5.63 mmol) of 2-chloro-4-methyl quinoline and 1.77 g (32.7 mmol) of sodium methoxide were dissolved in 12 mL of methanol, and the solution was heated to reflux for 16 hours to react. After the solution was cooled to a normal temperature, 30 mL of water was added thereto, and extracted with ethyl acetate (40 mL×once). The obtained organic phase was dried over sodium sulfate, the solvent was removed under reduced pressure to obtain 0.95 g of the target compound, 2-methoxy-4-methyl quinoline, as a colorless oily product.

Step 2

0.95 g (5.48 mmol) of 2-methoxy-4-methyl quinoline was dissolved in 10 mL of 1,2-dichloroethane, and then 1.17 g (6.58 mmol) of N-bromosuccinimide and 44 mg (0.27 mmol) of 2,2'-azobisisobutyronitrile were added, and stirred for 2 hours while heated at 90° C. After stirring was completed, the solution was cooled to a normal temperature, and the solvent was removed under reduced pressure to obtain 4-(bromomethyl)-2-methoxyquinoline. The obtained 4-(bromomethyl)-2-methoxyquinoline was used in a next step without any particular isolation and purification.

Step 3

The 4-(bromomethyl)-2-methoxyquinoline obtained in Step 2 was dissolved in 7 mL of acetonitrile, and then 0.5 g (1.54 mmol) of quinine was added, and stirred for 2 hours while heated at 70° C. After stirring was completed, the solution was cooled to a normal temperature, and 20 mL of diisopropyl ether was added. Then, the solution was filtered under reduced pressure to separate a solid precipitated in the reaction solution. The resultant residual solid was washed with a mixed solvent of 5 mL of chloroform and 15 mL of diisopropyl ether. After washing, the solid was dried under reduced pressure to obtain 0.82 g of the target compound, 2-methoxy-4-methyl quinoline quininium bromide. The melting point was 181° C. to 191° C. (degradation). M⁺496 was confirmed by LCMS.

Reaction Example

By using 2-methoxy-4-methyl quinoline quininium bromide instead of N-(acridin-9-ylmethyl)quininium bromide, a reaction was conducted in the same manner as in Example 1 to obtain (S)-4-(5-(3,5-dichlorophenyl)-5-trifluoromethyl-4,5-dihydroisoxazol-3-yl)-2-methyl benzamide with 79.5% ee of enantiomeric excess.

Example 8

Preparation of PTC: 2-chloro-4-methyl quinoline quininium bromide

By using 2-chloro-4-methyl quinoline as a starting material, a reaction was conducted in the same manner as in Steps 2 and 3 of Example 7 to obtain 2-chloro-4-methyl quinoline quininium bromide. The melting point was 181° C. to 191° C. (degradation). M⁺500 was confirmed by LCMS.

Reaction Example

By using 2-chloro-4-methyl quinoline quininium bromide instead of N-(acridin-9-ylmethyl)quininium bromide, a reaction was conducted in the same manner as in Example 1 to obtain (S)-4-(5-(3,5-dichlorophenyl)-5-trifluoromethyl-4,5-dihydroisoxazol-3-yl)-2-methyl benzamide with 74.0% ee of enantiomeric excess.

INDUSTRIAL APPLICABILITY

A production method of the present invention is useful as a method for catalytic asymmetric synthesis of an optically active isoxazoline compound. The optically active isoxazoline compound is a useful compound as an intermediate or a final technical product for agrochemicals, medicines, and functional materials.

The invention claimed is:
1. A method for catalytic asymmetric synthesis of an optically active isoxazoline compound, the method comprising:
causing an α,β-unsaturated carbonyl compound of Formula (1):

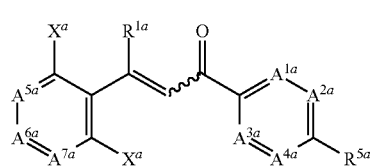

(1)

where $R^{1a}$ is $C_{1-6}$ fluoroalkyl or $C_{3-8}$ fluorocycloalkyl;
each of $A^{1a}$, $A^{2a}$, $A^{3a}$, and $A^{4a}$ is independently C—$Y^a$;
each of $A^{5a}$, $A^{6a}$, and $A^{7a}$ is independently C—$X^a$;
$X^a$ is a hydrogen atom, a halogen atom, cyano, nitro, —SF$_5$, $C_{1-6}$ alkyl, $C_{1-6}$ haloalkyl, hydroxy($C_{1-6}$)haloalkyl, $C_{1-6}$ alkoxy($C_{1-6}$)haloalkyl, $C_{1-6}$ haloalkoxy($C_{1-6}$)haloalkyl, $C_{3-8}$ halocycloalkyl, —OR$^{2a}$, —OSO$_2$R$^{2a}$, or —S(O)$_r$R$^{2a}$, and $X^a$s are optionally the same as or different from each other;

$R^{2a}$ is $C_{1-6}$ alkyl, $C_{1-4}$ alkoxy($C_{1-4}$)alkyl, $C_{1-6}$ haloalkyl, or $C_{1-3}$ haloalkoxy($C_{1-3}$)haloalkyl;

$Y^a$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-6}$ alkylthio, $C_{1-6}$ haloalkylthio, $C_{1-6}$ alkylsulfonyl, $C_{1-6}$ haloalkylsulfonyl, N(R$^{4a}$)R$^{3a}$ $Y^a$s are optionally the same as or different from each other, and when two $Y^a$s are adjacent to each other, the two $Y^a$s optionally form a 6-membered ring together with carbon atoms to which the two $Y^a$s are respectively bonded, by forming -A$^{8a}$=A$^{9a}$-A$^{10a}$=A$^{11a}$-;

each of $A^{8a}$, $A^{9a}$, $A^{10a}$, and $A^{11a}$ is independently N or C—$Y^{1a}$;

$Y^{1a}$ is a hydrogen atom, a halogen atom, cyano, nitro, $C_{1-4}$ alkyl, $C_{1-4}$ haloalkyl, $C_{1-4}$ alkoxy, $C_{1-4}$ haloalkoxy, $C_{1-6}$ alkylthio, $C_{1-6}$ haloalkylthio, $C_{1-6}$ alkylsulfonyl, $C_{1-6}$ haloalkylsulfonyl, N(R$^{4a}$)R$^{3a}$, and $Y^{1a}$s are optionally the same as or different from each other;

$R^{3a}$ is $C_{1-6}$ alkyl, $C_{1-6}$ alkylcarbonyl, $C_{1-6}$ haloalkylcarbonyl, $C_{1-6}$ alkoxycarbonyl, $C_{1-6}$ alkylthiocarbonyl, $C_{1-6}$ alkoxythiocarbonyl, $C_{1-6}$ alkyldithiocarbonyl, $C_{1-6}$ alkylsulfonyl, or $C_{1-6}$ haloalkylsulfonyl;

$R^{4a}$ is a hydrogen atom or $C_{1-6}$ alkyl;

$R^{5a}$ is —C(O)NH$_2$, —C(O)NHR$^{6a}$, —C(S)NHR$^{6a}$, or -L-NHR$^{6a}$;

$R^{6a}$ is $C_{1-6}$ alkyl, $C_{1-6}$ alkyl optionally substituted with R$^{9a}$, $C_{3-6}$ cycloalkyl optionally condensed with a benzene ring, $C_{3-6}$ alkenyl, $C_{3-6}$ haloalkenyl, $C_{3-6}$ alkynyl, —N(R$^{11a}$)R$^{10a}$, —C(O)OR$^{12a}$, —C(O)NH$_2$, —C(O)NHR$^{12a}$, —C(R$^{14a}$)=NOR$^{13a}$, phenyl, phenyl substituted with (Z)$_{p1}$, D-5, D-7, D-10, D-11, D-12, D-14, D-15, D-18, D-31, D-32, D-42, D-43, D-45, D-46, D-48, E-1, E-2, E-3, E-4, E-7, E-9 to E-20 or E-21;

$R^{9a}$ is a halogen atom, cyano, amino, $C_{3-6}$ cycloalkyl, $C_{3-6}$ halocycloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfonyl, $C_{1-6}$ haloalkylsulfinyl, $C_{1-6}$ alkylsulfonyl, $C_{1-6}$ haloalkylsulfonyl, —C(O)R$^{15a}$, —C(O)OR$^{15a}$, —C(O)NH$_2$, —C(O)N(R$^{16a}$)R$^{15a}$, —C(S)NH$_2$, —C(S)N(R$^{16a}$)R$^{15a}$, —C(R$^{18a}$)=NOR$^{17a}$, phenyl, phenyl substituted with (Z)$_{p1}$, D-1 to D-50, or E-1 to E-21;

D-1 to D-50 are heteroaromatic rings of structural formulae below:

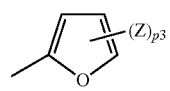

D-1

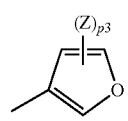

D-2

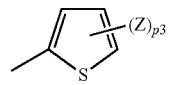

D-3

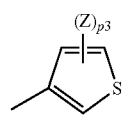

D-4

-continued
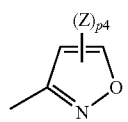 D-5
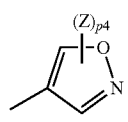 D-6
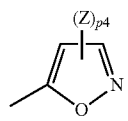 D-7
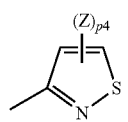 D-8
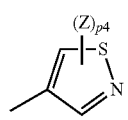 D-9
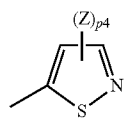 D-10
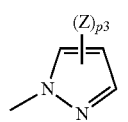 D-11
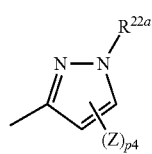 D-12
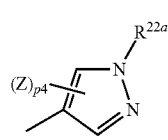 D-13
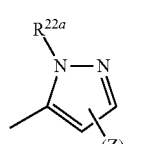 D-14
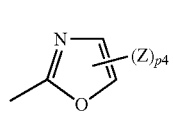 D-15
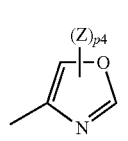 D-16
-continued
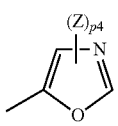 D-17
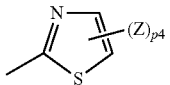 D-18
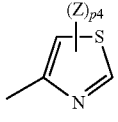 D-19
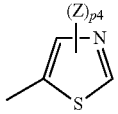 D-20
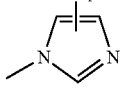 D-21
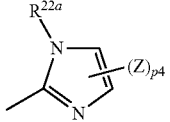 D-22
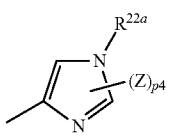 D-23
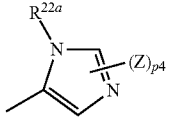 D-24
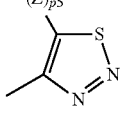 D-25
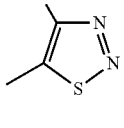 D-26
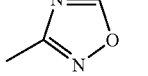 D-27
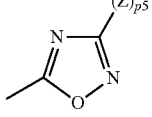 D-28

-continued

D-29 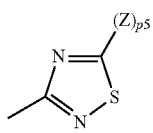

D-30 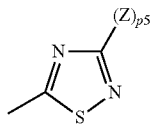

D-31 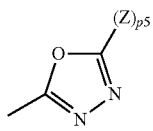

D-32 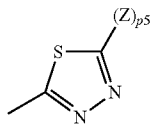

D-33 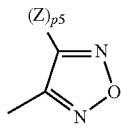

D-34 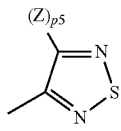

D-35 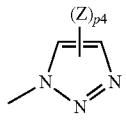

D-36 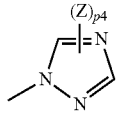

D-37 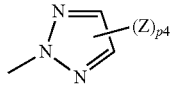

D-38 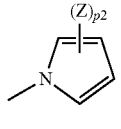

D-39 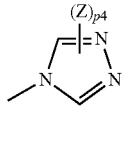

D-40 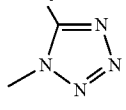

-continued

D-41 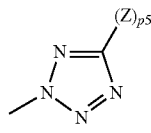

D-42 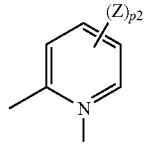

D-43 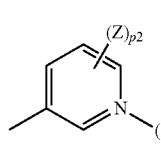

D-44 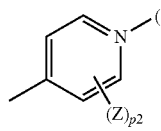

D-45 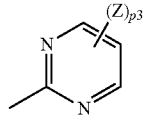

D-46 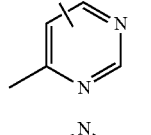

D-47 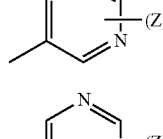

D-48 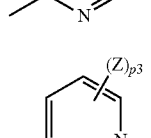

D-49 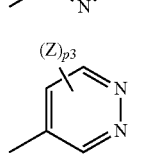

D-50 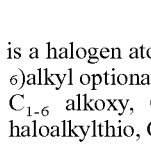

Z is a halogen atom, cyano, nitro, amino, $C_{1-6}$ alkyl, $(C_{1-6})$alkyl optionally substituted with $R^{19a}$, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ alkoxycarbonyl, —C(O)NH$_2$, —C(S)NH$_2$, —S(O)$_2$NH$_2$, —C(O)N(R$^{21a}$)R$^{20a}$, —C(S)N(R$^{21a}$)R$^{20a}$, $C_{1-6}$ alkylaminosulfonyl, or di($C_{1-6}$ alkyl)aminosulfonyl, and when p1, p2, p3, or p4 is an integer of 2 or more, Zs are optionally the same as or different from each other;

E-1 to E-21 are heterocycles of structural formulae below:

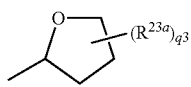 E-1

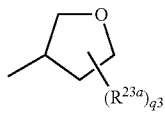 E-2

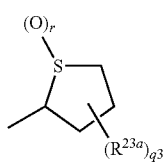 E-3

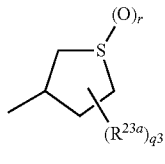 E-4

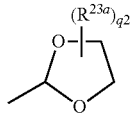 E-5

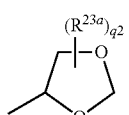 E-6

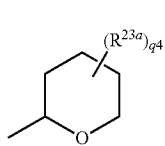 E-7

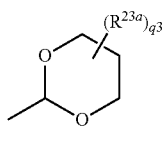 E-8

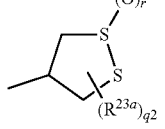 E-9

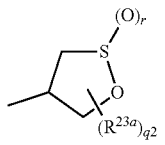 E-10

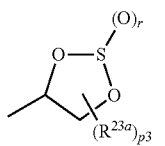 E-11

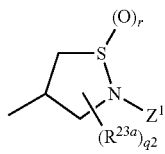 E-12

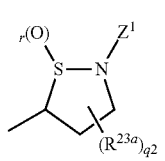 E-13

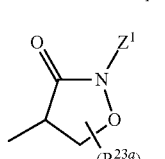 E-14

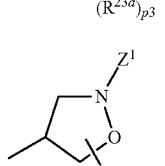 E-15

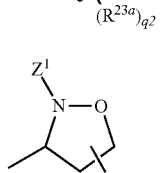 E-16

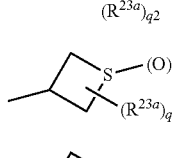 E-17

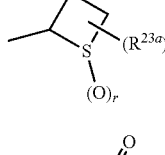 E-18

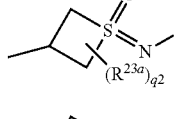 E-19

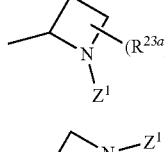 E-20

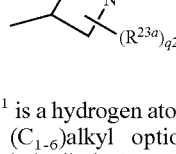 E-21

$Z^1$ is a hydrogen atom, $C_{1-6}$ alkyl, $C_{3-6}$ cycloalkyl, benzyl, $(C_{1-6})$alkyl optionally substituted with $R^{19a}$, $C_{1-6}$ haloalkyl, $C_{1-6}$ alkylcarbonyl, $C_{1-6}$ haloalkylcarbonyl, phenylcarbonyl, phenylcarbonyl substituted with $(Z)_{p1}$, $C_{1-6}$ alkoxycarbonyl, $C_{1-6}$ alkylsulfinyl, $C_{1-6}$ haloalkylsulfinyl, $C_{1-6}$ alkylsulfonyl, $C_{1-6}$ haloalkylsulfonyl, —C(O)NH$_2$, —C(S)NH$_2$, —S(O)$_2$NH$_2$, —C(O)N(R$^{21a}$)R$^{20a}$, C(S)N(R$^{21a}$)R$^{20a}$, $C_{1-6}$ alkylaminosulfonyl, di($C_{1-6}$ alkyl)aminosulfonyl, E-17, or E-18;

$Z^2$ is a hydrogen atom or $C_{1-6}$ haloalkylcarbonyl;

$R^{10a}$ is a $C_{1-6}$ haloalkyl, —C(O)$R^{15a}$, —C(O)O$R^{15a}$, phenyl, phenyl substituted with $(Z)_{p1}$, D-3, D-4, D-18, D-42, D-45, D-46, D-48, or D-49;

$R^{11a}$ is a hydrogen atom, $C_{1-6}$ alkyl, or $C_{3-6}$ alkynyl;

$R^{12a}$ is $C_{1-6}$ alkyl, $C_{1-6}$ haloalkyl, $C_{1-6}$ alkoxy($C_{1-4}$)alkyl, $C_{1-6}$ alkylthio($C_{1-4}$)alkyl, $C_{3-8}$ cycloalkyl, $C_{3-6}$ alkenyl, or $C_{3-6}$ alkynyl;

$R^{13a}$ is a hydrogen atom, $C_{1-6}$ alkyl, $C_{1-6}$ haloalkyl, $C_{3-6}$ cycloalkyl, $C_{3-6}$ halocycloalkyl, $C_{3-6}$ alkenyl, $C_{3-6}$ haloalkenyl, $C_{3-6}$ alkynyl, $C_{3-6}$ haloalkynyl, phenyl, phenyl substituted with $(Z)_{p1}$, D-42, D-45 to D-49, E-1 to E-4, or E-7;

$R^{14a}$ is a hydrogen atom, $C_{1-6}$ alkyl, $C_{1-6}$ haloalkyl, $C_{1-6}$ alkoxy($C_{1-6}$)alkyl, $C_{1-6}$ alkylthio($C_{1-6}$)alkyl, $C_{3-6}$ cycloalkyl, or phenyl;

$R^{15a}$ is $C_{1-6}$ alkyl, $C_{1-6}$ haloalkyl, $C_{3-6}$ cycloalkyl($C_{1-4}$)alkyl, $C_{3-6}$ cycloalkyl, $C_{1-6}$ alkoxy($C_{1-6}$)alkyl, hydroxy($C_{1-6}$)alkyl, phenyl, phenyl substituted with $R^{24a}$, $C_{3-6}$ haloalkenyl, $C_{3-6}$ alkenyl, or $C_{3-6}$ alkynyl;

$R^{24a}$ is a halogen atom, cyano, nitro, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, $C_{1-6}$ alkoxycarbonyl, —C(O)NH$_2$, —S(O)$_2$NH$_2$, $C_{1-6}$ alkylaminosulfonyl, or di($C_{1-6}$ alkyl)aminosulfonyl;

$R^{16a}$ is a hydrogen atom or $C_{1-6}$ alkyl;

$R^{19a}$ is hydroxy, $C_{1-4}$ alkoxy, or $C_{1-4}$ alkylthio;

$R^{20a}$ is a hydrogen atom, $C_{1-6}$ alkyl, $C_{3-6}$ cycloalkyl, $C_{3-6}$ alkenyl, $C_{3-6}$ haloalkenyl, $C_{3-6}$ alkynyl, —C($R^{17a}$)=NO$R^{18a}$, —C(O)O$R^{18a}$, —C(O)NH$_2$, —C(O)N($R^{17a}$)$R^{18a}$, —C(O)NHC(O)$R^{18a}$, —C(O)N($R^{17a}$)C(O)O$R^{18a}$, —N($R^{26a}$)$R^{25a}$, or phenyl;

$R^{17a}$ is a hydrogen atom or $C_{1-6}$ alkyl;

$R^{18a}$ is $C_{1-6}$ alkyl, $C_{1-6}$ haloalkyl, or $C_{2-6}$ alkenyl;

$R^{21a}$ is a hydrogen atom, $C_{1-6}$ alkyl, or $C_{3-6}$ alkynyl;

$R^{22a}$ is $C_{1-6}$ alkyl, phenyl, or phenyl substituted with $(Z)_{p1}$;

$R^{23a}$ is $C_{1-4}$ alkyl, and when q2, q3, or q4 is an integer of 2 or more, $R^{23a}$s are optionally the same as or different from each other, and further, when two of $R^{23a}$s exist on a single carbon atom as substituents, the two $R^{23a}$s optionally form an oxo together;

$R^{25a}$ is $C_{1-6}$ haloalkyl, $C_{1-6}$ alkoxycarbonyl, phenyl, phenyl substituted with $R^{27a}$, D-42 to D-46 or D-47;

$R^{27a}$ is a halogen atom, cyano, nitro, $C_{1-6}$ alkyl, $C_{1-6}$ haloalkyl, $C_{1-6}$ alkoxy, or $C_{1-6}$ alkylsulfonyl;

$R^{26a}$ is a hydrogen atom, $C_{1-6}$ alkyl, $C_{3-6}$ alkenyl, or $C_{3-6}$ alkynyl, p1 is an integer of 1 to 5;

p2 is an integer of 0 to 4;

p3 is an integer of 0 to 3;

p4 is an integer of 0 to 2;

p5 is an integer of 0 or 1;

q2 is an integer of 0 to 5;

q3 is an integer of 0 to 7;

q4 is an integer of 0 to 9;

t is an integer of 0 or 1;

L is —C($R^{7a}$)($R^{8a}$)—, —C($R^{7a}$)($R^{8a}$)CH$_2$—, or —CH$_2$C($R^{7a}$)($R^{8a}$)—;

$R^{7a}$ is a hydrogen atom, cyano, $C_{1-6}$ alkyl, $C_{1-6}$ haloalkyl, $C_{1-6}$ alkoxycarbonyl, —C(O)NH$_2$, or —C(S)NH$_2$;

$R^{8a}$ is a hydrogen atom or $C_{1-6}$ alkyl, or optionally forms a 3 to 6-membered ring together with carbon atoms bonded to a $C_{2-5}$ alkylene chain formed by $R^{7a}$ and $R^{8a}$, in which the alkylene chain optionally contains 1 to 3 oxygen atom(s), sulfur atom(s), or nitrogen atom(s); and r is an integer of 0 to 2, to react with a hydroxyl amine in a solvent, in the presence of a base and a chiral phase transfer catalyst of Formulae (7), (8), (9), or (10):

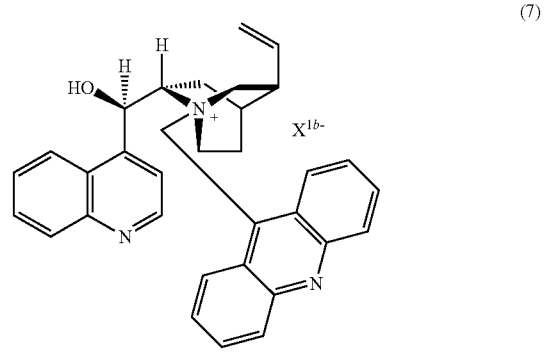

(7)

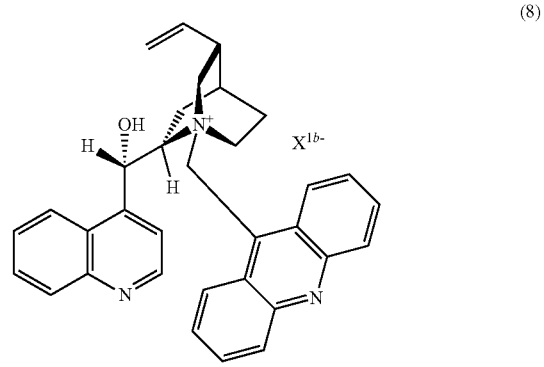

(8)

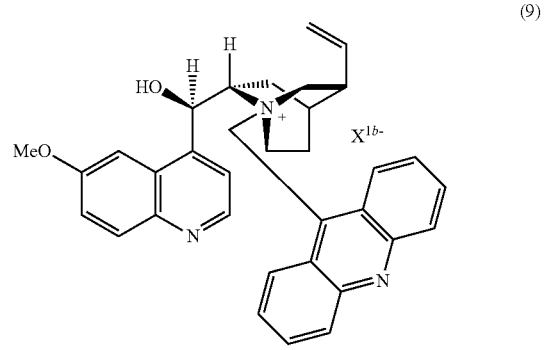

(9)

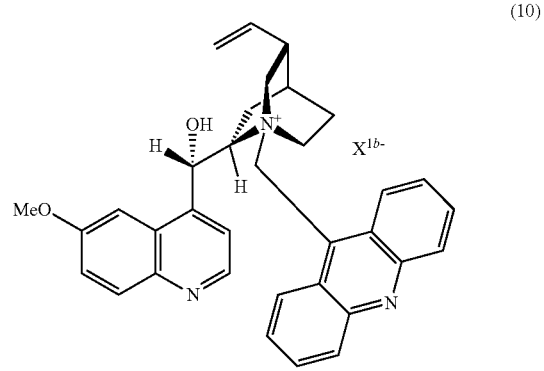

(10)

where $X^{1b-}$ is a negatively charged ion, wherein
the optically active isoxazoline compound is represented by Formula (6):

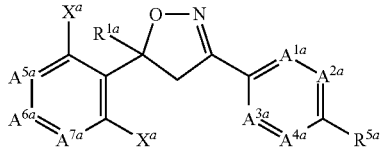

(6)

where each of $R^{1a}$, $R^{5a}$, $X^a$, $A^{1a}$, $A^{2a}$, $A^{3a}$, $A^{4a}$, $A^{5a}$, $A^{6a}$, and $A^{7a}$ is the same as that described above.

2. The method for catalytic asymmetric synthesis of an optically active isoxazoline compound, according to claim 1, wherein in Formula (1), $R^{6a}$ is $C_{1-6}$ alkyl, $C_{1-6}$ alkyl optionally substituted with $R^{9a}$, $C_{3-6}$ cycloalkyl optionally condensed with a benzene ring, $C_{3-6}$ alkenyl, $C_{3-6}$ haloalkenyl, $C_{3-6}$ alkynyl, —N($R^{11a}$)$R^{10a}$, —C(O)O$R^{12a}$, —C(O)NH$_2$, —C(O)NH$R^{12a}$, —C($R^{14a}$)=NO$R^{13a}$, phenyl, phenyl substituted with $(Z)_{p1}$, D-5, D-7, D-10, D-11, D-12, D-14, D-15, D-18, D-31, D-32, D-42, D-43, D-45, D-46, D-48, E-1, E-2, E-3, E-4, E-7, E-9 to E-16, E-19, E-20, or E-21; and $R^{9a}$ is a halogen atom, cyano, amino, $C_{3-6}$ cycloalkyl, $C_{3-6}$ halocycloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, —C(O)$R^{15a}$, —C(O)O$R^{15a}$, —C(O)NH$_2$, —C(O)N($R^{16a}$)$R^{15a}$, —C(S)NH$_2$, —C(S)N($R^{16a}$)$R^{15a}$, —C($R^{18a}$)=NO$R^{17a}$, phenyl, phenyl substituted with $(Z)_{p1}$, D-1 to D-50, E-1 to E-16, E-19, E-20, or E-21.

3. The method for catalytic asymmetric synthesis of an optically active isoxazoline compound, according to claim 1, wherein in Formula (1), $R^{1a}$ is —CF$_3$;

$Y^a$ is a hydrogen atom, or two adjacent $Y^a$s form —CH=CH—CH=CH— so as to form a 6-membered ring together with carbon atoms to which the two $Y^a$s are respectively bonded;

$A^{3a}$ is CH;

$A^{4a}$ is CH or C—CH$_3$;

$R^{6a}$ is $C_{1-6}$ alkyl, $C_{1-6}$ alkyl optionally substituted with $R^{9a}$, $C_{3-6}$ cycloalkyl optionally condensed with a benzene ring, $C_{3-6}$ alkenyl, $C_{3-6}$ haloalkenyl, $C_{3-6}$ alkynyl, —N($R^{11a}$)$R^{10a}$, —C(O)O$R^{12a}$, —C(O)NH$_2$, —C(O)NH$R^{12a}$, —C($R^{14a}$)=NO$R^{13a}$, phenyl, phenyl substituted with $(Z)_{p1}$, D-5, D-7, D-10, D-11, D-12, D-14, D-15, D-18, D-31, D-32, D-42, D-43, D-45, D-46, D-48, E-1, E-2, E-3, E-4, E-7, E-9 to E-16, E-19, E-20, or E-21; and $R^{9a}$ is a halogen atom, cyano, amino, $C_{3-6}$ cycloalkyl, $C_{3-6}$ halocycloalkyl, $C_{1-6}$ alkoxy, $C_{1-6}$ haloalkoxy, $C_{1-6}$ alkylthio, $C_{1-6}$ haloalkylthio, $C_{1-6}$ alkylsulfinyl, $C_{1-6}$ haloalkylsulfinyl, $C_{1-6}$ alkylsulfonyl, $C_{1-6}$ haloalkylsulfonyl, —C(O)$R^{15a}$, —C(O)O$R^{15a}$, —C(O)NH$_2$, —C(O)N($R^{16a}$)$R^{15a}$, —C(S)NH$_2$, —C(S)N($R^{16a}$)$R^{15a}$, —C($R^{18a}$)=NO$R^{17a}$, phenyl, phenyl substituted with $(Z)_{p1}$, D-1 to D-50, E-1 to E-16, E-19, E-20 or E-21.

4. The method for catalytic asymmetric synthesis of an optically active isoxazoline compound, according to claim 1, wherein in Formula (1), $R^{6a}$ is $C_1$ alkyl optionally substituted with $R^{9a}$, E-17, or E-18; and $R^{9a}$ is E-17 or E-18.

5. The method for catalytic asymmetric synthesis of an optically active isoxazoline compound, according to claim 1, wherein in Formulae (7), (8), (9), and (10), $X^{1b-}$ is a halogen ion, a hydroxide ion, a tetrafluoroborate, a hexafluorophosphate, an acetate, a triflate, a phenoxide or a sulfonic acid ion optionally substituted with a polystyrene.

* * * * *